United States Patent [19]

Jones et al.

[11] 4,133,814

[45] Jan. 9, 1979

[54] 2-PHENYL-3-AROYLBENZOTHIOPHENES USEFUL AS ANTIFERTILITY AGENTS

[75] Inventors: C. David Jones; Tulio Suarez, both of Indianapolis, Ind.

[73] Assignee: Eli Lilly and Company, Indianapolis, Ind.

[21] Appl. No.: 724,203

[22] Filed: Sep. 17, 1976

Related U.S. Application Data

[63] Continuation-in-part of Ser. No. 626,010, Oct. 28, 1975, abandoned.

[51] Int. Cl.² ............... C07D 409/10; C07D 333/56; A61K 31/38
[52] U.S. Cl. ............... 260/326.55 A; 260/330.5; 260/544 Y; 424/248.51; 424/267; 424/274; 424/275; 544/146; 546/202; 562/431

[58] Field of Search ..... 260/239 B, 293.57, 326.55 A, 260/330.5, 247.1 P; 544/146

[56] References Cited

U.S. PATENT DOCUMENTS

| | | | |
|---|---|---|---|
| 3,947,470 | 3/1976 | Brenner et al. | 260/330.5 |
| 3,983,245 | 9/1976 | Ladd et al. | 260/293.57 |
| 4,001,426 | 1/1977 | Brenner et al. | 260/293.57 |
| 4,007,204 | 7/1977 | Descamps et al. | 260/330.5 |

Primary Examiner—Nicholas S. Rizzo
Assistant Examiner—Mark L. Berch
Attorney, Agent, or Firm—William C. Martens, Jr.; Arthur R. Whale

[57] ABSTRACT

Derivatives of 2-phenyl-3-aroylbenzothiophenes and 2-phenyl-3-aroylbenzothiophene-1-oxides are useful as antifertility agents. Certain of these compounds also are useful in suppressing the growth of mammary tumors.

10 Claims, No Drawings

2-PHENYL-3-AROYLBENZOTHIOPHENES USEFUL AS ANTIFERTILITY AGENTS

CROSS REFERENCE

This application is a continuation-in-part of Application Ser. No. 626,010, filed Oct. 28, 1975, now abandoned.

BACKGROUND OF THE INVENTION

This invention relates to novel compounds. More particularly, this invention relates to novel compounds which possess valuable utility as antifertility agents and thus are useful in the control of animal populations. Also, certain of these compounds are active in the suppression of the growth of mammary tumors. In another aspect, this invention relates to a novel method of inhibiting pregnancy and to a novel method of controlling animal populations.

The prior art has recognized various classes of compounds, each having the general formula

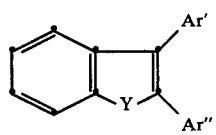

in which Ar is an aryl moiety and Y is any of various groups, such as —CH$_2$—, —CH$_2$-CH$_2$—, —S—, —NH, —OCH$_2$—, —O—, —CH$_2$S—, and —SCH$_2$—. Many compounds within these general classes are described as having antifertility activity.

Lednicer et al., J. Med. Chem., 8, (1965), pp. 52–57, discloses 2,3-diphenylindenes and derivatives thereof as antifertility agents.

Lednicer et al., J. Med. Chem., 9, (1966), pp. 172–175; Lednicer et al., J. Med. Chem., 10 (1967), pp. 78–84; and Bencze et al., J. Med. Chem., 8 (1965), pp. 213–214, each disclose various 1,2-diaryl-3,4-dihydronaphthalenes as active antifertility agents. In addition, U.S. Pat. Nos. 3,274,213; 3,313,853; 3,396,169; and 3,567,737 disclose various 1,2-diphenyl-3,4-dihydronaphthalenes as useful antifertility agents.

Other United States Patents disclose both 1,2-diphenyl-3,4-dihydronaphthalenes and 2,3-diphenylindenes as active agents. These include U.S. Pat. Nos. 3,293,263; 3,320,271; 3,483,293; 3,519,675; 3,804,851; and 3,862,232.

In addition, Crenshaw et al., J. Med. Chem. 14, (1971), pp. 1185–1190, discloses, among others, various 2,3-diarylbenzothiophenes as exhibiting antifertility activity. Certain of these compounds are claimed in U.S. Pat. No. 3,413,305. Crenshaw et al. additionally disclose other compounds which participate in the general classes described hereinabove. 2,3-Diarylbenzofurans corresponding generally to the above benzothiophenes are disclosed and claimed in U.S. Pat. No. 3,394,125.

A need still exists to provide additional compounds useful as antifertility agents and, in particular, nonsteroidal antifertility agents. The novel compounds of this invention fill such a need. They are 2-phenyl-3-aroylbenzothiophenes and 2-phenyl-3-aroylbenzothiophene-1-oxides, and, structurally, they differ significantly from those described in the aforementioned prior art. In addition, certain of these compounds are useful in suppressing the growth of mammary tumors. It is an object therefore of this invention to provide novel nonsteroidal compounds having antifertility activity and antitumor activity.

SUMMARY OF THE INVENTION

This as well as other objects are achieved by this invention which comprises a class of compounds having the formula

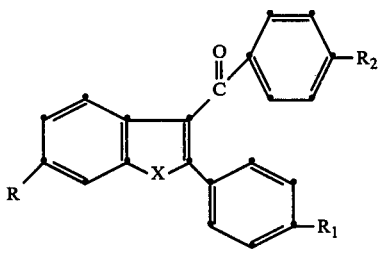

in which X is —S— or

R is hydrogen, hydroxyl, or C$_1$–C$_5$ alkoxy; R$_1$ is hydrogen, hydroxyl, C$_1$–C$_5$ alkoxy, C$_1$–C$_5$ acyloxy, C$_1$–C$_5$ alkoxycarbonyloxy, benzoyloxy, adamantoyloxy, chloro, bromo, or

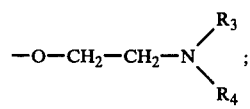

and R$_2$ is hydrogen, hydroxyl, C$_1$–C$_5$ alkoxy, or

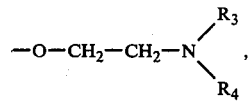

in any of the above of which R$_3$ and R$_4$ independently are C$_1$–C$_4$ alkyl, or R$_3$ and R$_4$ taken together with the nitrogen to which they are bonded constitute a heterocyclic ring selected from the group consisting of pyrrolidino, piperidino, hexamethyleneimino, or morpholino; subject to the limitation that when R$_2$ is hydrogen, R$_1$ is hydrogen, hydroxy, C$_1$–C$_5$ alkoxy, or

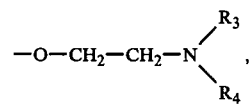

and at least one of R and R$_1$ is other than hydrogen; and pharmaceutically acceptable non-toxic acid addition salts of those compounds in which any of R$_1$ and R$_2$ are

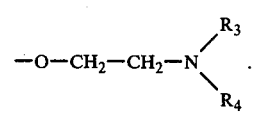

As indicated above, this invention also includes the pharmaceutically acceptable non-toxic acid addition salts of those of the above compounds in which $R_1$ and/or $R_2$ is

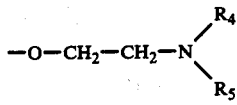

The pharmaceutically acceptable non-toxic acid addition salts include the organic and inorganic acid addition salts, for example, those prepared from acids such as hydrochloric, sulfuric, sulfonic, tartaric, fumaric, hydrobromic, glycolic, citric, maleic, phosphoric, succinic, acetic, nitric, and the like. Preferably, the acid addition salts are those prepared from citric acid. Such salts are prepared by conventional methods.

The term "$C_1$–$C_4$ alkyl" as used herein contemplates both straight and branched chain groups such as methyl, ethyl, n-propyl, isopropyl, n-butyl, t-butyl, isobutyl, and sec-butyl.

The term "$C_1$–$C_5$ alkoxy" as used herein contemplates both straight and branched chain alkyl radicals and therefore defines groups such as, for example, methoxy, ethoxy, n-propoxy, isopropoxy, n-butyloxy, isobutyloxy, t-butyloxy, sec-butyloxy, n-amyloxy, isoamyloxy, t-amyloxy, sec-amyloxy, and the like.

The term "$C_1$–$C_5$ acyloxy" as used herein contemplates, for example, formyloxy, acetoxy, propionoxy, butyroxy, and valeroxy.

The term "$C_1$–$C_5$ alkoxycarbonyloxy" as used herein contemplates, for example, methoxycarbonyloxy, ethoxycarbonyloxy, propoxycarbonyloxy, butoxycarbonyloxy, and pentyloxycarbonyloxy.

A preferred subclass of the compounds of this invention are the benzothiophenes, that is, in the above formula, those compounds in which X is —S—.

Of the defined benzothiophenes, several preferred subclasses exist. One such subclass is comprised of the compounds of the above formula in which X, R, and $R_1$ are as defined, and $R_2$ is

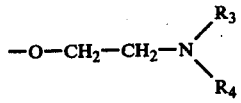

Another preferred subclass comprises those compounds in which $R_2$ is hydrogen and either R is hydroxyl or $R_1$ is

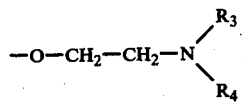

A further preferred subclass comprises those compounds in which $R_2$ is hydroxyl and $R_1$ is other than hydroxyl or $C_1$–$C_5$ alkoxy. An additional preferred subclass are those compounds in which $R_2$ is $C_1$–$C_5$ alkoxy, R is hydrogen or $C_1$–$C_5$ alkoxy, and $R_1$ is hydrogen or

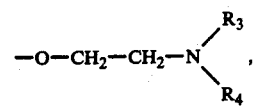

with the proviso that no more than one of R and $R_1$ is hydrogen. A further preferred subclass are those compounds in which $R_2$ is $C_1$–$C_5$ alkoxy and both R and $R_1$ are hydroxyl.

In those instances in which $R_1$ and/or $R_2$ is

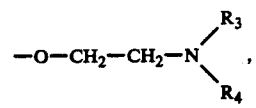

it is further preferred that both $R_3$ and $R_4$ are methyl, both $R_3$ and $R_4$ are ethyl, or $R_3$ and $R_4$ taken together with the nitrogen to which they are bonded constitute a pyrrolidino ring.

Certain of the compounds of this invention can be prepared by a number of varied sequences. These compounds then can be converted to others within the broad teaching of this invention. The general sequences can be summarized as follows:

A. Acylation of 2-phenylbenzothiophenes.

A benzothiophene of the formula

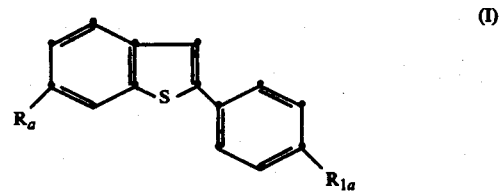

in which $R_a$ is hydrogen, $C_1$–$C_5$ alkoxy, phenacyloxy, or p-halophenacyloxy, and $R_{1a}$ is hydrogen, $C_1$–$C_5$ alkoxy, chloro, bromo, phenacyloxy, or p-halophenacyloxy, is reacted with a benzoyl chloride of the formula

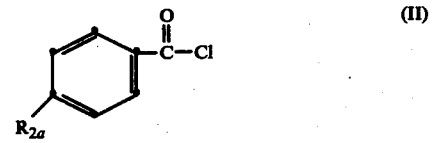

in which $R_{2a}$ is hydrogen, $C_1$–$C_5$ alkoxy, phenacyloxy, or p-halophenacyloxy.

The reaction is carried out using equimolar quantities of the reactants in an inert organic solvent and in the presence of an equivalent of aluminum chloride or any other suitable Lewis acid catalyst. Generally, the reaction is conducted with cooling, usually at about 0° C. to about 5° C.

The product which is obtained is a compound of this invention. This compound either is itself active as an antifertility agent or is useful as an intermediate to such an active compound. The compound which is produced has the formula

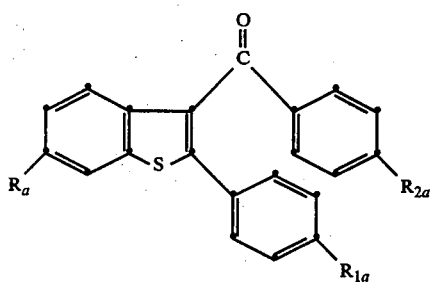

in which $R_a$, $R_{1a}$, and $R_{2a}$ are as defined above.

B. From 2,3-Dioxo-2,3-dihydrobenzothiophenes.

Another sequence for preparing the compounds of Formula III is by way of a compound of the formula

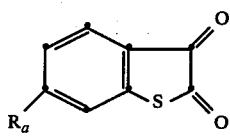

Compound IV is available from the thiophenol

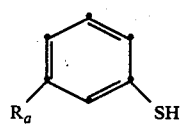

by either of two sequences. The thiophenol is heated with bromoacetic acid to produce

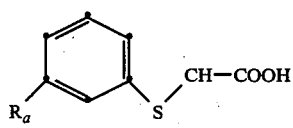

This can then be ring-closed in the presence of polyphosphoric acid at a moderately elevated temperature to produce the tautomeric 3-hydroxybenzothiophene of the formula

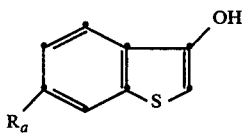

which then is converted to compound IV by reaction with p-nitroso-N,N-dimethylaniline and hydrolysis of the resulting intermediate Schiff's base.

Alternatively, the thiophenol (V) can be treated with oxalyl chloride to produce the intermediate

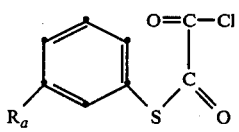

which, without being isolated, is ring-closed to compound IV in the presence of aluminum chloride.

The compound IV, by whichever route it is obtained, is converted to

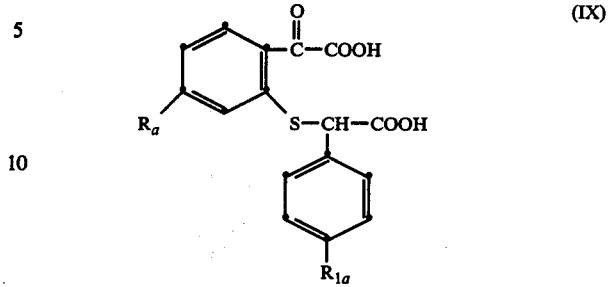

by reaction with α-chlorophenylacetic acid or an appropriately substituted derivative thereof.

The diacid (IX) is cyclized with a mixture of sodium acetate and acetic anhydride to

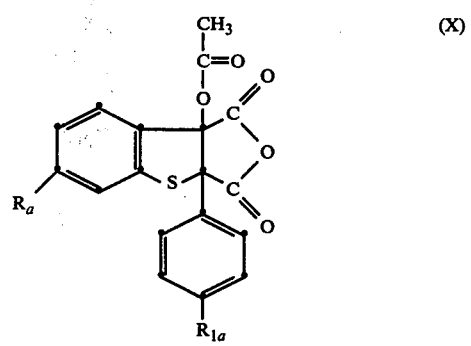

which is then hydrolyzed in the presence of sodium hydroxide to

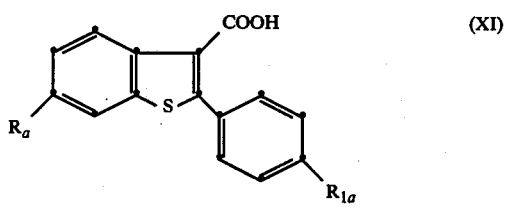

Conversion of XI to the acid chloride by treatment with thionyl chloride and reaction of the acid chloride with

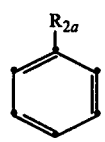

in the presence of a Lewis acid catalyst such as aluminum chloride, or with

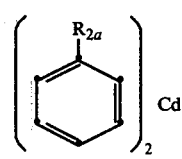

produces compound III, a compound of this invention.

C. Preparation of compounds in which R, $R_1$, and/or $R_2$ is hydroxyl.

These compounds are prepared from Compound III above in which those of $R_a$, $R_{1a}$, and $R_{2a}$ intended ultimately to be hydroxyl are methoxy, phenacyloxy, or p-halophenacyloxy.

Treatment of the Compound III with pyridine hydrochloride at reflux produces the corresponding hydroxyl compound in which each $R_a$, $R_{1a}$, and/or $R_{2a}$ group which was methoxy in the starting material has been cleaved to its corresponding hydroxyl function.

Selective cleavage of the methoxy groups can be accomplished by the use of reagents which preferentially attack a methoxy group located at a particular position of the molecule. Thus, if it is desired to cleave a methoxy group at $R_{2a}$ while retaining intact a methoxy at $R_a$ and/or $R_{1a}$, this can be accomplished using sodium thioethoxide. The benzothiophene is reacted with sodium thioethoxide in an inert solvent at a moderately elevated temperature of from about 50° C. to about 80° C. for a period sufficient to accomplish the desired reaction. The ongoing of the reaction can be monitored by periodic thin-layer chromatographic analysis (TLC) of the reaction mixture. The reaction is complete when little or no starting benzothiophene remains.

When the methoxy group to be cleaved is located at $R_a$ and/or $R_{1a}$, this can be accomplished without affecting a methoxy at $R_{2a}$ by reacting the benzothiophene with boron tribromide. The reaction is carried out in an inert solvent, preferably methylene chloride. In the event that a methoxy group is present at both $R_a$ and $R_{1a}$, the product which results will be dependent upon both the time and temperature of the reaction. When the reaction is carried out for an extended period, for example, 20–36 hours at room temperature, both methoxy groups will be cleaved to the dihydroxy compound. This can be modified by shortening the reaction time, in which case a mixture of products will result representing cleavage either of the methoxy at $R_a$ or the methoxy at $R_{1a}$. In this event the desired product can be separated from the mixture by employing standard techniques, such as chromatographic separation.

Alternatively, R, $R_1$, and/or $R_2$ of the final product can be hydroxyl by use during synthesis of a suitable hydroxyl protecting group. Thus, for example, $R_a$, $R_{1a}$, and/or $R_{2a}$ can be phenacyloxy or p-halophenacyloxy, such as p-chlorophenacyloxy or p-bromophenacyloxy. The phenacyl portion of any of these groups can be readily cleaved to produce the corresponding hydroxyl derivative by treatment with zinc and acetic acid at about 60° C. for approximately one hour. The particular sequence of synthetic steps designed to produce a compound having substituents of particular definition and location is such as one of ordinary skill in the art will well recognize.

D. Preparation of compounds in which $R_1$ and/or $R_2$ is

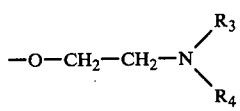

These compounds can be produced by reacting the corresponding hydroxy compound prepared as aforedescribed with a compound of the formula

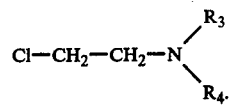

The reaction is carried out in the presence of sodium hydride at a moderately elevated temperature of about 60° C. to about 80° C., and the progress of the reaction can be monitored by TLC.

Alternatively, the group

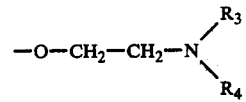

can already be present on the phenyl moiety to be added to the benzothiophene. Thus, the following sequences are available:

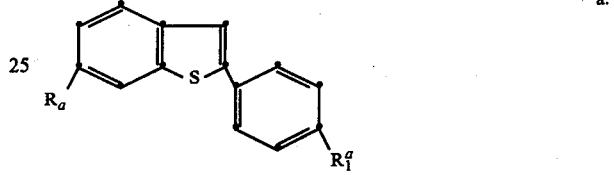

a.

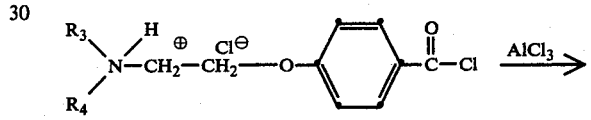

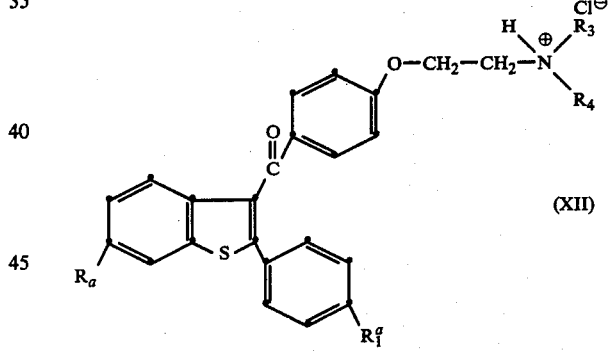

(XII)

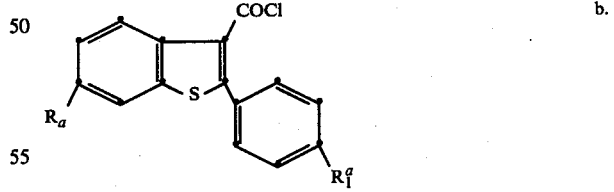

b.

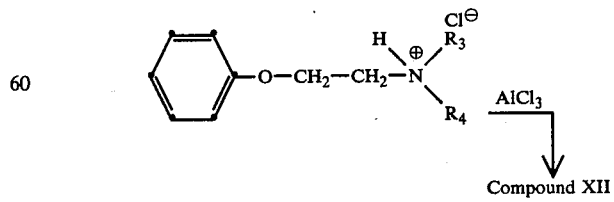

Compound XII

The product can be isolated in the form of its free base. However, it can also be converted by treatment with an appropriate acid to its pharmaceutically acceptable non-toxic acid addition salt. This latter can be accomplished merely by treating the free base, either isolated or while in the reaction mixture, and in accordance with routine techniques, with the acid of the desired pharmaceutically acceptable salt.

E. Preparation of the compounds in which $R_1$ is acyloxy.

In those instances in which $R_1$ is $C_1$–$C_5$ acyloxy, such a compound can be obtained by reacting the corresponding hydroxy compound with the appropriate acyl chloride.

F. Preparation of compounds in which X is

These compounds are readily available by oxidation of any of the benzothiophenes produced as described above. Oxidation can be carried out by treating the benzothiophene with an oxidizing agent, for example, m-chloroperbenzoic acid, or the like, for a time sufficient to achieve formation of the sulfoxide group. The ongoing of the reaction can be monitored by standard thin-layer chromatography (TLC) methods.

The compounds of this invention are valuable pharmaceutical agents or intermediates thereto. Those which are pharmaceutical agents exhibit anti-fertility activity, and they especially are useful as orally active anti-fertility agents in birds and mammals. The compounds of this invention thus are useful in controlling the animal population and as contraceptives in living beings. The compounds of the invention also are valuable for animal pest control. For example, the compounds of this invention can be formulated in combination with baits and/or attractants and placed in feeding stations accessible to undesirable rodents and other small animals including Canidae such as coyotes, foxes, wolves, jackals, and wild dogs, and birds, such as starlings, galls, redwing blackbirds, pigeons, and the like, to greatly reduce the population thereof. By reason of the activity of the compounds of this invention, they can be used to reduce hazards to aviation by lessening the presence of birds and animals on runways and in the vicinity of air fields. The compounds of this invention also can be used to reduce the population of undesirable birds and animals so as to aid in the prevention and the spread of disease, and to reduce the destruction of property in both rural and urban areas.

In addition, certain of the compounds of this invention are active in suppressing the growth of mammary tumors. In general, the compounds of this invention which are active anti-tumor agents are those benzothiophenes in which $R_2$ is the group

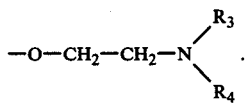

When so employed, it is preferred that the compounds be administered parenterally.

The compounds of this invention can be administered as such, or they can be compounded and formulated into pharmaceutical preparations in unit dosage form for oral or parenteral administration. In the compounding or formulation, organic or inorganic solids and/or liquids which are pharmaceutically acceptable carriers can be employed. Suitable such carriers will be well recognized by those of ordinary skill in the art. The compositions may take the form of tablets, powder granules, capsules, suspensions, solutions, and the like.

The compounds of this invention, when administered in an effective amount, will inhibit pregnancy in mammals and certain of them will inhibit tumor growth. The usual daily dose for antifertility or anti-tumor purposes is from about 0.04 milligrams to about 20 milligrams per kilogram body weight of the recipient. The preferred antifertility daily dose is from about 0.04 milligrams to about 0.4 milligrams per kilogram body weight of the recipient. The preferred daily dose for treating mammary tumors is from about 0.04 milligrams to about 8 milligrams per kilogram body weight of the recipient.

Examples of compounds of this invention include the following:
2-(4-hydroxyphenyl)-3-benzoylbenzothiophene;
2-(4-methoxyphenyl)-3-benzoylbenzothiophene;
2-(4-isopropoxyphenyl)-3-benzoylbenzothiophene;
2-(4-t-butyloxyphenyl)-3-benzoylbenzothiophene;
2-(4-pentyloxyphenyl)-3-benzoylbenzothiophene;
2-[4-(2-dimethylaminoethoxy)phenyl]-3-benzoylbenzothiophene;
2-[4-(2-diethylaminoethoxy)phenyl]-3-benzoylbenzothiophene;
2-[4-(2-pyrrolidinoethoxy)phenyl]-3-benzoylbenzothiophene;
2-[4-(2- piperidinoethoxy)phenyl]-3-benzoylbenzothiophene;
2-[4-(2-hexamethyleneiminoethoxy)phenyl]-3-benzoylbenzothiophene;
2-[4-(2-morpholinoethoxy)phenyl]-3-benzoylbenzothiophene;
2-(4-ethoxyphenyl)-3-benzoylbenzothiophene;
2-phenyl-3-benzoyl-6-hydroxybenzothiophene;
2-phenyl-3-benzoyl-6-methoxybenzothiophene;
2-phenyl-3-benzoyl-6-ethoxybenzothiophene;
2-phenyl-3-benzoyl-6-isopropoxybenzothiophene;
2-phenyl-3-benzoyl-6-n-propoxybenzothiophene;
2-phenyl-3-benzoyl-6-n-butoxybenzothiophene;
2-phenyl-3-benzoyl-6-isobutoxybenzothiophene;
2-phenyl-3-benzoyl-6-t-butóxybenzothiophene;
2-phenyl-3-benzoyl-6-pentyloxybenzothiophene;
2-(4-hydroxyphenyl)-3-benzoyl-6-hydroxybenzothiophene;
2-(4-methoxyphenyl)-3-benzoyl-6-methoxybenzothiophene;
2-(4-hydroxyphenyl)-3-benzoyl-6-methoxybenzothiophene;
2-(4-methoxyphenyl)-3-benzoyl-6-hydroxybenzothiophene;
2-[4-(2-pyrrolidinoethoxy)phenyl]-3-benzoyl-6-methoxybenzothiophene;
2-[4-(2-dimethylaminoethoxy)phenyl]-3-benzoyl-6-hydroxybenzothiophene;
2-[4-(2-piperidinoethoxy)phenyl]-3-benzoyl-6-ethoxybenzothiophene;
2-(4-isopropoxyphenyl)-3-benzoyl-6-propoxybenzothiophene;
2-phenyl-3-(4-hydroxybenzoyl)benzothiophene;
2-(4-hydroxyphenyl)-3-(4-hydroxybenzoyl)benzothiophene;
2-(4-methoxyphenyl)-3-(4-hydroxybenzoyl)benzothiophene;
2-(4-ethoxyphenyl)-3-(4-hydroxybenzoyl)benzothiophene;

2-(4-t-butoxyphenyl)-3-(4-hydroxybenzoyl)benzothiophene;
2-(4-formyloxyphenyl)-3-(4-hydroxybenzoyl)benzothiophene;
2-(4-acetoxyphenyl)-3-(4-hydroxybenzoyl)benzothiophene;
2-(4-propionoxyphenyl)-3-(4-hydroxybenzoyl)benzothiophene;
2-(4-chlorophenyl)-3-(4-hydroxybenzoyl)benzothiophene;
2-(4-bromophenyl)-3-(4-hydroxybenzoyl)benzothiophene;
2-[4-(2-pyrrolidinoethoxy)phenyl]-3-(4-hydroxybenzoyl)benzothiophene;
2-[4-(2-dimethylaminoethoxy)phenyl]-3-(4-hydroxybenzoyl)benzothiophene;
2-(4-hydroxyphenyl)-3-(4-methoxybenzoyl)benzothiophene;
2-(4-methoxyphenyl)-3-(4-methoxybenzoyl)benzothiophene;
2-(4-propoxyphenyl)-3-(4-methoxybenzoyl)benzothiophene;
2-(4-acetoxyphenyl)-3-(4methoxybenzoyl)benzothiophene;
2-(4-bromophenyl)-3-(4-methoxybenzoyl)benzothiophene;
2-[4-(2-pyrrolidinoethoxy)phenyl]-3-(4-methoxybenzoyl)benzothiophene;
2-[4-(2-morpholinoethoxy)phenyl]-3-(4-methoxybenzoyl)benzothiophene;
2-(4-hydroxyphenyl)-3-(4-t-butoxybenzoyl)benzothiophene;
2-[4-(2-piperidinoethoxy)phenyl]-3-(4-t-butoxybenzoyl)benzothiophene;
2-(4-ethoxyphenyl)-3-(4-ethoxybenzoyl)benzothiophene;
2-(4-methoxyphenyl)-3-[4-(2-dimethylaminoethoxy)benzoyl]benzothiophene;
2-(4-hydroxyphenyl)-3-[4-(2-dimethylaminoethoxy)benzoyl]benzothiophene;
2-[4-(2-dimethylaminoethoxy)phenyl]-3-[4-(2-dimethylaminoethoxy)benzoyl]benzothiophene;
2-[4-(2-pyrrolidinoethoxy)phenyl]-3-[4-(2-pyrrolidinoethoxy)benzoyl]benzothiophene;
2-phenyl-3-[4-(2-pyrrolidinoethoxy)benzoyl]-6-hydroxybenzothiophene;
2-phenyl-3-[4-(2-pyrrolidinoethoxy)benzoyl]-6-methoxybenzothiophene;
2-phenyl-3-[4-(2-pyrrolidinoethoxy)benzoyl]-6-propoxybenzothiophene;
2-phenyl-3-(4-hydroxybenzoyl)-6-hydroxybenzothiophene;
2-phenyl-3-(4-methoxybenzoyl)-6-hydroxybenzothiophene;
2-phenyl-3-(4-methoxybenzoyl)-6-methoxybenzothiophene;
2-phenyl-3-(4-ethoxybenzoyl)-6-hydroxybenzothiophene;
2-phenyl-3-(4-ethoxybenzoyl)-6-ethoxybenzothiophene;
2-phenyl-3-(4-pentyloxybenzoyl)-6-hydroxybenzothiophene;
2-phenyl-3-(4-pentyloxybenzoyl)-6-methoxybenzothiophene;
2-phenyl-3-(4-pentyloxybenzoyl)-6-n-propoxybenzothiophene;
2-(4-hydroxyphenyl)-3-(4-pentyloxybenzoyl)-6-hydroxybenzothiophene;
2-(4-methoxyphenyl)-3-(4-hydroxybenzoyl)-6-hydroxybenzothiophene;
2-(4-n-propoxyphenyl)-3-(4-hydroxybenzoyl)-6-methoxybenzothiophene;
2-(4-hydroxyphenyl)-3-(4-hydroxybenzoyl)-6-hydroxybenzothiophene;
2-(4-ethoxyphenyl)-3-(4-hydroxybenzoyl)-6-ethoxybenzothiophene;
2-(4-formyloxyphenyl)-3-(4-hydroxybenzoyl)-6-hydroxybenzothiophene;
2-(4-acetoxyphenyl)-3-(4-hydroxybenzoyl)-6-methoxybenzothiophene;
2-(4-propionoxyphenyl)-3-(4-hydroxybenzoyl)-6-t-butoxybenzothiophene;
2-(4-chlorophenyl)-3-(4-hydroxybenzoyl)-6-methoxybenzothiophene;
2-(4-bromophenyl)-3-(4-hydroxybenzoyl)-6-ethoxybenzothiophene;
2-[4-(2-di-n-propylaminoethoxy)phenyl]-3-(4-hydroxybenzoyl)-6-methoxybenzothiophene;
2-[4-(2-piperidinoethoxy)phenyl]-3-(4-hydroxybenzoyl)-6-methoxybenzothiophene;
2-[4-(2-hexamethyleneiminoethoxy)phenyl]-3-(4-hydroxybenzoyl)-6-methoxybenzothiophene;
2-(4-methoxyphenyl)-3-(4-methoxybenzoyl)-6-methoxybenzothiophene;
2-(4-hydroxyphenyl)-3-(4-methoxybenzoyl)-6-methoxybenzothiophene;
2-(4-hydroxyphenyl)-3-(4-methoxybenzoyl)-6-hydroxybenzothiophene;
2-(4-isopropoxyphenyl)-3-(4-methoxybenzoyl)-6-methoxybenzothiophene;
2-(4-acetoxyphenyl)-3-(4-methoxybenzoyl)-6-ethoxybenzothiophene;
2-(4-bromophenyl)-3-(4-methoxybenzoyl)-6-hydroxybenzothiophene;
2-[4-(2-diethylaminoethoxy)phenyl]-3-(4-methoxybenzoyl)-6-propoxybenzothiophene;
2-[4-(2-dibutylaminoethoxy)phenyl]-3-(4-methoxybenzoyl)-6-hydroxybenzothiophene;
2-(4-methoxyphenyl)-3-(4-ethoxybenzoyl)-6-hydroxybenzothiophene;
2-(4-hydroxyphenyl)-3-(4-ethoxybenzoyl)-6-methoxybenzothiophene;
2-[4-(2-pyrrolidinoethoxy)phenyl]-3-(4-ethoxybenzoyl)-6-pentyloxybenzothiophene;
2-[4-(2-piperidinoethoxy)phenyl]-3-(4-n-propoxybenzoyl)-6-methoxybenzothiophene;
2-(4-methoxyphenyl)-3-(4-t-butoxybenzoyl)-6-hydroxybenzothiophene;
2-(4-hydroxyphenyl)-3-(4-pentyloxybenzoyl)-6-methoxybenzothiophene;
2-(4-hydroxyphenyl)-3-[4-(2-dimethylaminoethoxy)benzoyl]-6-hydroxybenzothiophene;
2-(4-chlorophenyl)-3-[4-(2-dimethylaminoethoxy)benzoyl]-6-methoxybenzothiophene;
2-(4-methoxyphenyl)-3-[4-(2-dimethylaminoethoxy)benzoyl]-6-methoxybenzothiophene;
2-(4-formyloxyphenyl)-3-[4-(2-dimethylaminoethoxy)benzoyl]-6-hydroxybenzothiophene;
2-[4-(2-dimethylaminoethoxy)phenyl]-3-[4-(2-dimethylaminoethoxy)benzoyl]-6-hydroxybenzothiophene;
2-[4-(2-dimethylaminoethoxy)phenyl]-3-[4-(2-dimethylaminoethoxy)benzoyl]-6-methoxybenzothiophene;
2-(4-hydroxyphenyl)-3-[4-(2-pyrrolidinoethoxy)benzoyl]-6-hydroxybenzothiophene;

2-(4-methoxyphenyl)-3-[4-(2-pyrrolidinoethoxy)benzoyl]-6-methoxybenzothiophene;
2-[4-(2-pyrrolidinoethoxy)phenyl]-3-[4-(2-pyrrolidinoethoxy)benzoyl]-6-propoxybenzothiophene;
2-(4-chlorophenyl)-3-[4-(2-diethylaminoethoxy)benzoyl]-6-hydroxybenzothiophene;
2-(4-methoxyphenyl)-3-[4-(2-diethylaminoethoxy)benzoyl]-6-t-butoxybenzothiophene;
2-[4-(2-diethylaminoethoxy)phenyl]-3-[4-(2-diethylaminoethoxy)benzoyl]-6-pentyloxybenzothiophene;
2-[4-(2-diethylaminoethoxy)phenyl]-3-[4-(2-diethylaminoethoxy)benzoyl]-6-methoxybenzothiophene;
2-phenyl-3-(4-hydroxybenzoyl)-6-methoxybenzothiophene;
2-phenyl-3-(4-hydroxybenzoyl)-6-ethoxybenzothiophene;
2-(4-hydroxyphenyl)-3-benzoylbenzothiophene-1-oxide;
2-(4-methoxyphenyl)-3-benzoylbenzothiophene-1-oxide;
2-(4-isopropoxyphenyl)-3-benzoylbenzothiophene-1-oxide;
2-(4-t-butyloxyphenyl)-3-benzoylbenzothiophene-1-oxide;
2-(4-pentyloxyphenyl)-3-benzoylbenzothiophene-1-oxide;
2-[4-(2-dimethylaminoethoxy)phenyl]-3-benzoylbenzothiophene-1-oxide;
2-[4-(2-diethylaminoethoxy)phenyl]-3-benzoylbenzothiophene-1-oxide;
2-[4-(2-pyrrolidinoethoxy)phenyl]-3-benzoylbenzothiophene-1-oxide;
2-[4-(2-piperidinoethoxy)phenyl]-3-benzoylbenzothiophene-1-oxide;
2-[4-(2-hexamethyleneiminoethoxy)phenyl]-3-benzoylbenzothiophene-1-oxide;
2-[4-(2-morpholinoethoxy)phenyl]-3-benzoylbenzothiophene-1-oxide;
2-(4-ethoxyphenyl)-3-benzoylbenzothiophene-1-oxide;
2-phenyl-3-benzoyl-6-hydroxybenzothiophene-1-oxide;
2-phenyl-3-benzoyl-6-methoxybenzothiophene-1-oxide;
2-phenyl-3-benzoyl-6-ethoxybenzothiophene-1-oxide;
2-phenyl-3-benzoyl-6-isopropoxybenzothiophene-1-oxide;
2-phenyl-3-benzoyl-6-n-propoxybenzothiophene-1-oxide;
2-phenyl-3-benzoyl-6-n-butoxybenzothiophene-1-oxide;
2-phenyl-3-benzoyl-6-isobutoxybenzothiophene-1-oxide;
2-phenyl-3-benzoyl-6-t-butoxybenzothiophene-1-oxide;
2-phenyl-3-benzoyl-6-pentyloxybenzothiophene-1-oxide;
2-(4-hydroxyphenyl)-3-benzoyl-6-hydroxybenzothiophene-1-oxide;
2-(4-methoxyphenyl)-3-benzoyl-6-methoxybenzothiophene-1-oxide;
2-(4-hydroxyphenyl)-3-benzoyl-6-methoxybenzothiophene-1-oxide;
2-(4-methoxyphenyl)-3-benzoyl-6-hydroxybenzothiophene-1-oxide;
2-[4-(2-pyrrolidinoethoxy)phenyl]-3-benzoyl-6-methoxybenzothiophene-1-oxide;
2-[4-(2-dimethylaminoethoxy)phenyl]-3-benzoyl-6-hydroxybenzothiophene-1-oxide;
2-[4-(2-piperidinoethoxy)phenyl]-3-benzoyl-6-ethoxybenzothiophene-1-oxide;
2-(4-isopropoxyphenyl)-3-benzoyl-6-propoxybenzothiophene-1-oxide;
2-phenyl-3-(4-hydroxybenzoyl)benzothiophene-1-oxide;
2-(4-hydroxyphenyl)-3-(4-hydroxybenzoyl)benzothiophene-1-oxide;
2-(4-methoxyphenyl)-3-(4-hydroxybenzoyl)benzothiophene-1-oxide;
2-(4-ethoxyphenyl)-3-(4-hydroxybenzoyl)benzothiophene-1-oxide;
2-(4-t-butoxyphenyl)-3-(4-hydroxybenzoyl)benzothiophene-1-oxide;
2-(4-formyloxyphenyl)-3-(4-hydroxybenzoyl)benzothiophene-1-oxide;
2-(4-acetoxyphenyl)-3-(4-hydroxybenzoyl)benzothiophene-1-oxide;
2-(4-propionoxyphenyl)-3-(4-hydroxybenzoyl)benzothiophene-1-oxide;
2-(4-chlorophenyl)-3-(4-hydroxybenzoyl)benzothiophene-1-oxide;
2-(4-bromophenyl)-3-(4-hydroxybenzoyl)benzothiophene-1-oxide;
2-[4-(2-pyrrolidinoethoxy)phenyl]-3-(4-hydroxybenzoyl)benzothiophene-1-oxide;
2-[4-(2-dimethylaminoethoxy)phenyl]-3-(4-hydroxybenzoyl)benzothiophene-1-oxide;
21 -(4-hydroxyphenyl)-3-(4-methoxybenzoyl)benzothiophene-1-oxide;
2-(4-methoxyphenyl)-3-(4-methoxybenzoyl)benzothiophene-1-oxide;
2-(4-propoxyphenyl)-3-(4-methoxybenzoyl)benzothiophene-1-oxide;
2-(4-acetoxyphenyl)-3-(4-methoxybenzoyl)benzothiophene-1-oxide;
2-(4-bromophenyl)-3-(4-methoxybenzoyl)benzothiophene-1-oxide;
2-[4-(2-pyrrolidinoethoxy)phenyl]-3-4-methoxybenzoyl)benzothiophene-1-oxide;
2-[4-(2-morpholinoethoxy)phenyl]-3(4-methoxybenzoyl)benzothiophene-1-oxide;
2-(4-hydroxyphenyl)-3-(4-t-butoxybenzoyl)benzothiophene-1-oxide;
2-[4-(2-piperidinoethoxy)phenyl]-3-(4-t-butoxybenzoyl)benzothiophene-1-oxide;
2-(4-ethoxyphenyl)-3-(4-ethoxybenzoyl)benzothiophene-1-oxide;
2-(4-methoxyphenyl)-3-[4-(2-dimethylaminoethoxy)benzoyl]benzothiophene-1-oxide;
2-(4-hydroxyphenyl)-3-[4-(2-dimethylaminoethoxy)benzoyl]benzothiophene-1-oxide;
2-[4-(2-dimethylaminoethoxy)phenyl]-3-[4-(2-dimethylaminoethoxy)benzoyl]benzothiophene-1-oxide;
2-[4-(2-pyrrolidinoethoxy)phenyl]-3-[4-(2-pyrrolidinoethoxy)benzoyl]benzothiophene-1-oxide;
2-phenyl-3-[4-(2-pyrrolidinoethoxy)benzoyl]-6-hydroxybenzothiophene-1-oxide;
2-phenyl-3-[4-(2-pyrrolidinoethoxy)benzoyl]-6-methoxybenzothiophene-1-oxide;
2-phenyl-3-[4-(2-pyrrolidinoethoxy)benzoyl]-6-propoxybenzothiophene-1-oxide;
2-phenyl-3-(4-hydroxybenzoyl)-6-hydroxybenzothiophene-1-oxide;
2-phenyl-3-(4-methoxybenzoyl)-6-hydroxybenzothiophene-1-oxide;
2-phenyl-3-(4-methoxybenzoyl)-6-methoxybenzothiophene-1-oxide;
2-phenyl-3-(4-ethoxybenzoyl)-6-hydroxybenzothiophene-1-oxide;

2-phenyl-3-(4-ethoxybenzoyl)-6-ethoxybenzothiophene-1-oxide;
2-phenyl-3-(4-pentyloxybenzoyl)-6-hydroxybenzothiophene-1-oxide;
2-phenyl-3-(4-pentyloxybenzoyl)-6-methoxybenzothiophene-1-oxide;
2-phenyl-3-(4-pentyloxybenzoyl-6-n-propoxybenzothiophene-1-oxide;
2-(4-hydroxyphenyl)-3-(4-pentyloxybenzoyl)-6-hydroxybenzothiophene-1-oxide;
2-(4-methoxyphenyl)-3-(4-hydroxybenzoyl)-6-hydroxybenzothiophene-1-oxide;
2-(4-n-propoxyphenyl)-3-(4-hydroxybenzoyl)-6-methoxybenzothiophene-1-oxide;
2-(4-hydroxyphenyl)-3-(4-hydroxybenzoyl)-6-hydroxybenzothiophene-1-oxide;
2-(4-ethoxyphenyl)-3-(4-hydroxybenzoyl)-6-ethoxybenzothiophene-1-oxide;
2-(4-formyloxyphenyl)-3-(4-hydroxybenzoyl)-6-hydroxybenzothiophene-1-oxide;
2-(4-acetoxyphenyl)-3-(4-hydroxybenzoyl)-6-methoxybenzothiophene-1-oxide;
2-(4-propionoxyphenyl)-3-(4-hydroxybenzoyl)-6-t-butoxybenzothiophene-1-oxide;
2-(4-chlorophenyl)-3-(4-hydroxybenzoyl)-6-methoxybenzothiophene-1-oxide;
2-(4-bromophenyl)-3-(4-hydroxybenzoyl)-6-ethoxybenzothiophene-1-oxide;
2-[4-(2-di-n-propylaminoethoxy)phenyl]-3-(4-hydroxybenzoyl)-6-methoxybenzothiophene-1-oxide;
2-[4-(2-piperidinoethoxy)phenyl]-3-(4-hydroxybenzoyl)-6-methoxybenzothiophene-1-oxide;
2-[4-(2-hexamethyleneiminoethoxy)phenyl]-3-(4-hydroxybenzoyl)-6-methoxybenzothiophene-1-oxide;
2-(4-methoxyphenyl)-3-(4-methoxybenzoyl)-6-methoxybenzothiophene-1-oxide;
2-(4-hydroxyphenyl)-3-(4-methoxybenzoyl)-6-methoxybenzothiophene-1-oxide;
2-(4-hydroxyphenyl)-3-(4-methoxybenzoyl)-6-hydroxybenzothiophene-1-oxide;
2-(4-isopropoxyphenyl)-3-(4-methoxybenzoyl)-6-methoxybenzothiophene-1-oxide;
2-(4-acetoxyphenyl)-3-(4-methoxybenzoyl)-6-ethoxybenzothiophene-1-oxide;
2-(4-bromophenyl)-3-(4-methoxybenzoyl)-6-hydroxybenzothiophene-1-oxide;
2-[4-(2-diethylaminoethoxy)phenyl]-3-(4-methoxybenzoyl)-6-propoxybenzothiophene-1-oxide;
2-[4-(2-dibutylaminoethoxy)phenyl]-3-(4-methoxybenzoyl)-6-hydroxybenzothiophene-1-oxide;
2-(4-methoxyphenyl)-3-(4-ethoxybenzoyl)-6-hydroxybenzothiophene-1-oxide;
2-(4-hydroxyphenyl)-3-(4-ethoxybenzoyl)-6-methoxybenzothiophene-1-oxide;
2-[4-(2-pyrrolidinoethoxy)phenyl]-3-(4-ethoxybenzoyl)-6-pentyloxybenzothiophene-1-oxide;
2-[4-(2-piperidinoethoxy)phenyl]-3-(4-n-propoxybenzoyl)-6-methoxybenzothiophene-1-oxide;
2-(4-methoxyphenyl)-3-(4-t-butoxybenzoyl)-6-hydroxybenzothiophene-1-oxide;
2-(4-hydroxyphenyl)-3-(4-pentyloxybenzoyl)-6-methoxybenzothiophene-1-oxide;
2-(4-hydroxyphenyl)-3-[4-(2-dimethylaminoethoxy)benzoyl]-6-hydroxybenzothiophene-1-oxide;
2-(4-chlorophenyl)-3-[4-(2-dimethylaminoethoxy)benzoyl]-6-methoxybenzothiophene-1-oxide;
2-(4-methoxyphenyl)-3-[4-(2-dimethylaminoethoxy)benzoyl]-6-methoxybenzothiophene-1-oxide;
2-(4-formyloxyphenyl)-3-[4-(2-dimethylaminoethoxy)benzoyl]-6-hydroxybenzothiophene-1-oxide;
2-[4-(2-dimethylaminoethoxy)phenyl]-3-[4-(2-dimethylaminoethoxy)benzoyl]-6-hydroxybenzothiophene-1-oxide;
2-[4-(2-dimethylaminoethoxy)phenyl]-3-[4-(2-dimethylaminoethoxy)benzoyl]-6-methoxybenzothiophene-1-oxide;
2-(4-hydroxyphenyl)-3-[4-(2-pyrrolidinoethoxy)benzoyl]-6-hydroxybenzothiophene-1-oxide;
2-(4-methoxyphenyl)-3-[4-(2-pyrrolidinoethoxy)benzoyl]-6-methoxybenzothiophene-1-oxide;
2-[4-(2-pyrrolidinoethoxy)phenyl]-3-[4-(2-pyrrolidinoethoxy)benzoyl]-6-propoxybenzothiophene-1-oxide;
2-(4-chlorophenyl)-3-[4-(2-diethylaminoethoxy)benzoyl]-6-hydroxybenzothiophene-1-oxide;
2-(4-methoxyphenyl)-3-[4-(2-diethylaminoethoxy)benzoyl]-6-t-butoxybenzothiophene-1-oxide;
2-[4-(2-diethylaminoethoxy)phenyl]-3-[4-(2-diethylaminoethoxy)benzoyl]-6-pentyloxybenzothiophene-1-oxide;
2-[4-(2-diethylaminoethoxy)benzoyl]-6-methoxybenzothiophene-1-oxide;
2-phenyl-3-(4-hydroxybenzoyl)-6-methoxybenzothiophene-1-oxide;
2-phenyl-3-(4-hydroxybenzoyl)-6-ethoxybenzothiophene-1-oxide;
and the like.

The following examples are illustrative of the preparation and activities of the compounds of this invention. They are not intended to be limiting upon the broad scope thereof.

Preparation of Typical Key Intermediates

A. 2-Phenylbenzothiophene

To 300 ml. of pyridine were added 150 g. (0.75 mole) of α-bromoacetophenone and 83 g. (0.75 mole) of thiophenol. The mixture was heated at reflux for six hours. The pyridine then was evaporated, and the residue was dissolved in ethyl acetate. The ethyl acetate solution was washed exhaustively with 1N sodium hydroxide and 1N hydrochloric acid, dried over magnesium sulfate, filtered, and evaporated to a brown oil. The brown oil was crystallized from alcohol at 0° C. to give 116 g. (68 percent) of α-(phenylthio)acetophenone as white crystals, m.p. 52°–53° C.

Analysis, Calcd for $C_{14}H_{12}OS$: C, 73.65; H, 5.30; O, 7.01; S, 14.04. Found: C, 73.46; H, 5.50; O, 7.25; S, 14.30.

The above product was cyclized with accompanying isomerization of the phenyl group from the 3- to the 2-position of the benzothiophene product as follows: α-(phenylthio)acetophenone (63.8 g.) was added to 450 g. of polyphosphoric acid at 100° C. The mixture then was heated to 190° C. for 3 hours. Ice then was added to the reaction mixture. The product was extracted from the mixture with ether. The ether was dried over magnesium sulfate, and then was evaporated to a tan solid. The product was recrystallized from a mixture of acetone and alcohol to obtain 35.2 g. (60 percent) of the title compound, melting point 171°–172° C.

B. 2-(4-Methoxyphenyl)benzothiophene

A mixture of 45.8 g. (0.2 mole) of p-methoxyphenacyl bromide and 22.0 g. of thiophenol in ethanol was prepared. The mixture was stirred, and a solution of 12 g. of potassium hydroxide in 30 ml. of water was added dropwise. After approximately 30 minutes of stirring, a solid precipitated. The solid was collected by filtration and dissolved in ether. The solution was dried, concentrated, cooled, and filtered to obtain α-(phenylthio)-4-methoxyacetophenone, melting point 83°–85° C.

Analysis, Calcd. for $C_{15}H_{14}O_2S$: C, 69.74; H, 5.46. Found: C, 69.52; H, 5.48.

The product was cyclized with isomerization as in Preparation A by heating it in an oil bath with polyphosphoric acid at a temperature up to about 110° C. The mixture was stirred and maintained for one hour at about 100°–110° C. The mixture then was cooled, and water was added. The aqueous mixture then was extracted with chloroform, and the chloroform layer was separated, dried, and concentrated. A solid precipitated from the mixture and was separated by filtration to obtain 6.0 g. of the title compound, melting point 188°–190° C. The product was purified by recrystallization from ethanol.

Analysis, Calcd. for $C_{15}H_{12}OS$: C, 74.97; H, 5.03; O, 6.66 Found: C, 74.69; H, 5.19; O, 6.75.

C. 2-(4-Methoxyphenyl)-6-methoxybenzothiophene

To 700 ml. of ethanol were added 50.0 g. (0.356 mole) of m-methoxythiophenol. To the mixture then were added 20 g. (0.36 mole) of potassium hydroxide pellets followed by 82.5 g. (0.36 mole) of α-bromo-4-methoxyacetophenone added in small portions. The entire addition was carried out at about 25° C. Upon completion of the addition, the reaction mixture was stirred for three hours at room temperature. The ethanol then was evaporated, and a brown residual oil was taken up in two liters of water and 1.5 liters of ether. The ether layer was separated, washed with water, dried over magnesium sulfate, and evaporated. The resulting crystalline residue was homogenized in a blender using a 3:1 mixture of ether and petroleum ether. The solid was filtered and dried to give 78.5 g. (76 percent) of α-(3-methoxyphenylthio)-4-methoxyacetophenone as pink crystals, melting point 53°–54° C.

Analysis, Calcd. for $C_{16}H_{16}O_3S$: C, 66.64; H, 5.59; O, 16.64; S, 11.12 Found: C, 66.55; H, 5.87; O, 16.82; S, 10.86

The above product was cyclized with isomerization by adding 50 g. (0.173 mole) of the product to 250 g. of polyphosphoric acid preheated to about 95° C. The mixture was vigorously stirred, and the temperature rose to about 115°–120° C. Monitoring by TLC indicated that the reaction was over in about 5 minutes. At the end of 30 minutes, ice was added to the mixture. The temperature then rose to about 130° C. at which time additional ice was added. Crystals appeared; water was added to the mixture, and the product was collected by filtration. The resulting tan solid was slurried in hot methanol, cooled, and filtered. The solid was recrystallized from 2.5 l. of ethyl acetate to obtain 30 g. of the title compound, melting point 193°–194° C.

Analysis Calcd. for $C_{16}H_{14}O_2S$: C, 71.08; H, 5.22; O, 11.84; S. 11.86. Found: C, 71.03; H, 5.30; O, 11.81; S, 11.60.

EXAMPLE 1

Preparation of 2-Phenyl-3-(4-methoxybenzoyl)-benzothiophene.

To 75 ml. of 1,2-dichloroethane were added 7.0 g. (0.033 mole) of 2-phenylbenzothiophene and 5.80 g. (0.034 mole) of 4-anisoyl chloride. The mixture was cooled to 0° C., and 4.65 g. (0.035 mole) of aluminum chloride were added. The mixture was stirred for one hour and ice then was added. The resulting organic layer was separated, washed with water and evaporated. To the residue were added 250 ml. of methanol and 10 ml. of 5N sodium hydroxide. The mixture was refluxed for 30 minutes, evaporated, and ether and water were added to the residue. The ether layer was separated and was washed with 1N sodium hydroxide, 1N hydrochloric acid, and aqueous sodium chloride. The ether layer then was dried over magnesium sulfate, filtered, and evaporated. The residue was recrystallized from methanol with the aid of charcoal to give 7.7 g. (67 percent) of 2-phenyl-3-(4-methoxybenzoyl)benzothiophene as light tan crystals, melting point 107°–109° C. Mass spectrum: Theory, 344; Found, 344.

EXAMPLE 2

Preparation of 2-Phenyl-3-(4-hydroxybenzoyl)-benzothiophene.

A mixture of 4.0 g. (0.012 mole) of the product from Example 1 and 20 g. of pyridine hydrochloride was prepared. The mixture was refluxed for one hour.

The hot reaction mixture then was poured over an ice-water mixture in a blender, and the resulting crystals were collected. The crystals then were dissolved in ethyl acetate, and the ethyl acetate solution was washed with saturated aqueous sodium chloride and dried over magnesium sulfate. The ethyl acetate then was rapidly chromatographed over silica using ethyl acetate as eluant. The ethyl acetate eluant was evaporated to obtain a tan oil which slowly crystallized on standing. The crystalline product was recrystallized from a mixture of methanol and water and vacuum dried to give 2.79 g. (73 percent) of the title compound as pale tan crystals, melting point 163°–165° C.

Analysis, Calcd. for $C_{21}H_{14}O_2S$: C, 76.34; H, 4.27; O, 9.68; S, 9.70. Found: C, 76.31; H, 4.48; O, 9.76; S, 9.70. Mass spectrum: Theory, 330; Found, 330.

EXAMPLE 3

Preparation of 2-Phenyl-3-benzoyl-6-methoxybenzothiophene

A mixture of 100 g. (0.788 mole) of oxalyl chloride in 100 ml. of 1,2-dichloroethane was prepared. The solution was maintained at 25° C., and a mixture of 25 g. (0.179 mole) of m-methoxythiophenol in 50 ml. of 1,2-dichloroethane was added dropwise. Upon completion of addition, the mixture was refluxed for one hour and then was allowed to stir overnight. The solvent and the excess oxalyl chloride then were evaporated, and 100 ml. of fresh 1,2-dichloroethane were added. The mixture was cooled to 0° C., and 23.8 g. (0.178 mole) of aluminum chloride were added in three portions. The mixture was stirred for 15 minutes, and ice was added. 1,2-Dichloroethane was evaporated from the mixture, and yellow-orange crystals formed and were collected. The crystals were dried at 40° C. in vacuo to obtain 31.2 g. (89 percent) of 6-methoxy-2,3-dioxo-2,3-dihydrobenzothiophene. An analytical sample was recrystallized from a mixture of methanol and water to obtain pure product, melting point 165°–166° C.

The above dioxobenzothiophene (31.0 g.; 0.159 mole) and 24.8 g. (0.234 mole) of sodium carbonate were added to 350 ml. of boiling water. To the mixture while hot was added a solution of 79.4 g. (0.466 mole) of α-chlorophenylacetic acid and 37.0 g. (0.349 mole) of sodium carbonate in 500 ml. of water. This latter solution was previously prepared at 0° C. Upon completion of the addition, the reaction mixture was heated for five minutes, activated charcoal was added, and the mixture was cooled to 30° C. The mixture then was filtered, and the filtrate was acidified by addition of 100 ml. of 12N hydrochloric acid. A yellow oil precipitated which, upon standing, crystallized. The mixture was homogenized in a blender, washed with water, filtered, and vacuum dried at 35°–40° C. to obtain 53.9 g. (98 percent) of α-(2-carboxycarbonyl-5-methoxyphenylthio)-phenylacetic acid.

Analysis, Calcd. for $C_{17}H_{14}O_6S$: C, 58.95; H, 4.07; O, 27.72; S, 9.26 Found: C, 58.83; H, 4.13; O, 27.89; S, 9.03.

A mixture of 53 g. (0.153 mole) of the above phenylacetic acid and 63 g. (0.765 mole) of anhydrous sodium acetate in 780 g. (7.65 mole) of acetic anhydride was prepared. The mixture was stirred, heated slowly to reflux, and maintained at reflux for 15 minutes. The excess acetic anhydride then was hydrolyzed by careful dropwise addition of 1 l. of water. The resulting mixture was poured over ice and diluted to 3.5 l. by addition of ice. A brown precipitate formed and was collected and washed well with cold water. The resulting wet solid was used in the next succeeding step without further purification. Analysis of a sample of the product indicated it to be a mixture of the desired 2-phenyl-3-carboxyl-6-methoxybenzothiophene and its precursor, 2-phenyl-3-acetoxy-6-methoxy-2,3-dihydrobenzothiophene-2,3-dicarboxylic acid anhydride.

The wet product obtained above was refluxed in a mixture of 700 ml. of 2N sodium hydroxide and 250 ml. of ethanol for 20 minutes. The ethanol then was evaporated, ice and water were added, and the mixture was acidified by addition of 250 ml. of 6N hydrochloric acid at 0° C. A tan solid resulted and was collected by filtration. The tan solid was recrystallized from methanol to obtain 31.2 g. (71 percent) of 2-phenyl-3-carboxyl-6-methoxybenzothiophene, m.p. 196°–199° C.

Analysis, Calcd. for $C_{16}H_{12}O_3S$: C, 67.59; H, 4.25; O, 16.88; S, 11.28. Found: C, 67.38; H, 4.47; O, 16.85; S, 11.16.

Mass spectrum: Theory, 284; Found, 284.

The above product (10.0 g.; 0.0352 mole) was converted to the corresponding acid chloride by stirring it with 8.3 g. (0.07 mole) of thionyl chloride and two drops of pyridine in 200 ml. of anhydrous ether at 25° C. for 12 hours. The ether and excess thionyl chloride then was evaporated. To the residue were added 50 ml. of benzene, the mixture was evaporated to dryness, and the benzene treatment was repeated.

The resulting acid chloride was dissolved in 100 ml. of dry ether. A suspension of diphenylcadmium (prepared by addition at 25° C. of 5.7 g. (0.031 mole) of cadmium chloride to 100 ml. of ethyl ether containing 0.07 mole of phenylmagnesium bromide) was added. Upon completion of the addition, the mixture was refluxed for 15 minutes. Ice then was added to the mixture, and the resulting ether layer was separated and washed successively with 1N hydrochloric acid, 1N sodium hydroxide, and aqueous sodium chloride. The ether then was dried over magnesium sulfate and evaporated to obtain 12.3 g. of yellow crystals. The crystals were recrystallized from a mixture of 200 ml. of benzene and 40 ml. of hexane. A first crop (6.4 g.) and a second crop (2.2 g.), amounting to a 71 percent yield, were obtained. An analytical sample of the product, 2-phenyl-3-benzoyl-6-methoxybenzothiophene, was recrystallized, melting point 108°–110° C.

Analysis, Calcd. for $C_{22}H_{16}O_2S$: C, 76.72; H, 4.68; O, 9.29; S, 9.31. Found: C, 76.65; H, 4.92; O, 9.56; S, 9.33.

Mass spectrum: Theory, 344; Found, 344.

EXAMPLE 4

Preparation of 2-Phenyl-3-benzoyl-6-hydroxybenzothiophene.

A mixture of 6.0 g. (0.017 mole) of the product from Example 3 and 25 g. of pyridine hydrochloride was prepared. The mixture was refluxed for one hour, treated, and chromatographed as in Example 2 to obtain yellow crystals. The crystals were dissolved in hot acetone, methanol was added, and the acetone was boiled off. The residual mixture was evaporated to a volume of about 100 ml., and 10 ml. of hot water were added. The mixture was cooled and scratched to obtain 4.4 g. (76 percent) of 2-phenyl-3-benzoyl-6-hydroxybenzothiophene as yellow-gold crystals, melting point 221°–222° C.

Analysis, Calcd. for $C_{21}H_{14}O_2S$: C, 76.34; H, 4.27; O, 9.68; S, 9.70 Found: C, 76.18; H, 4.39; O, 9.40; S, 9.85.

EXAMPLE 5

Preparation of 2-Phenyl-3-(4-methoxybenzoyl)-6-methoxybenzothiophene.

Employing the procedure of Example 3, 10.0 g. (0.0352 mole) of 2-phenyl-3-carboxyl-6-methoxybenzothiophene were prepared and converted to the corresponding acid chloride.

The resulting acid chloride was dissolved in 150 ml. of 1,2-dichloroethane. To the solution were added 3.89 g. (0.036 mole) of anisole. The mixture was cooled to 0° C., and 4.80 g. (0.036 mole) of aluminum chloride were added. The mixture was stirred at 0° C. for one hour. Ice then was added to the mixture, and the organic layer was separated, washed with water, dried over magnesium sulfate, and evaporated to give a yellow oil which crystallized from methanol to obtain 11.60 g. (88 percent) of the title compound as nearly colorless crystals, melting point 132°–132.5° C.

Analysis, Calcd. for $C_{23}H_{18}O_3S$: C, 73.77; H, 4.85; O, 12.82; S, 8.56. Found: C, 74.02; H, 4.97; O, 13.05; S, 8.38.

EXAMPLE 6

Preparation of 2-Phenyl-3-(4-hydroxybenzoyl)-6-hydroxybenzothiophene.

Employing the demethylation procedure described in Example 2, 7.0 g. (0.0187 mole) of the product from Example 5 were demethylated to obtain 5.72 g. (88 percent) of the title compound, melting point 245°–246° C.

Analysis, Calcd. for $C_{21}H_{14}O_3S$: C, 72.81; H, 4.07; O, 13.86; S, 9.26. Found: C, 72.58; H, 4.24; O, 13.82; S, 9.40.

Mass spectrum: Theory, 346; Found, 346.

EXAMPLE 7

Preparation of 2-(4-methoxyphenyl)-3-benzoyl-6-methoxybenzothiophene.

To 300 ml. of 1,2-dichloroethane maintained at 0° C. were added 6.0 g. (0.022 mole) of 2-(4-methoxyphenyl)-6-methoxybenzothiophene and 3.10 g. (0.022 mole) of benzoyl chloride. The mixture was stirred vigorously, and 3.2 g. (0.024 mole) of aluminum chloride were added in small portions. The resulting red solution was stirred for one hour, and water then was added. The yellow organic layer was separated, washed with 200 ml. of 1N sodium hydroxide and then with 200 ml. of saturated sodium chloride solution. The mixture then was dried over potassium carbonate, and the solvent was evaporated to give a pale yellow solid which was purified by chromatography over silica gel using benzene and 5% ethyl acetate in benzene as eluant. The appropriate fractions gave product as yellow crystals. The product was recrystallized from methanol to obtain 3.5 g. (42 percent) of 2-(4-methoxyphenyl)-3-benozyl-6-methoxybenzothiophene, melting point 110.5°–111° C.

EXAMPLE 8

Preparation of 2-(4-Hydroxyphenyl)-3-benzoyl-6-hydroxybenzothiophene.

The product (2.5 g.; 0.0067 mole) from Example 7 was demethylated in accordance with the procedure described in Example 2 using 10 g. of pyridine hydrochloride to give 2.1 g. (91 percent) of the title compound, melting point 203°–205° C. (dec.)

Analysis Calcd. for $C_{21}H_{14}O_3S$: C, 72.81; H, 4.07; O, 13.86; S, 9.26 Found: C, 72.54; H, 4.09; O, 13.80; S, 9.23

Mass spectrum: Theory, 346; Found, 346.

EXAMPLE 9

Preparation of 2-(4-Methoxyphenyl)-3-(4-methoxybenzoyl)-6-methoxybenzothiophene

A mixture of 10.0 g. (0.037 mole) of 2-(4-methoxyphenyl)-6-methoxybenzothiophene in 700 ml. of 1,2-dichloroethane was prepared. The mixture was cooled to 0° C., and a mixture of 6.31 g. (0.037 mole) of 4-anisoyl chloride and 5.07 g. (0.038 mole) of aluminum chloride in 1,2-dichloroethane was added dropwise. The mixture was stirred at about 0° C. for two hours. The mixture then was poured into a mixture of ice and water. The organic layer was separated from the aqueous, and the aqueous layer was extracted with chloroform. The chloroform was added to the organic layer which was washed with aqueous sodium bicarbonate and then with water. The organic extract then was dried over magnesium sulfate and evaporated to obtain the crude reaction product as an oil. The oil was dissolved in 500 ml. of methanol, and 15 ml. of 5N sodium hydroxide were added. The resulting mixture was refluxed for 30 minutes and the methanol then was evaporated. The residue was extracted into ether, and the ether layer was washed with aqueous sodium chloride followed by water. The ether layer was separated and evaporated to obtain 14.6 g. of a yellow oily crude product. Purification by chromatography gave 13.9 g. (93 percent) of 2-(4-methoxyphenyl)-3-(4-methoxybenzoyl)-6-methoxybenzothiophene as a yellow oil.

Analysis, Calcd. for $C_{24}H_{20}O_4S$: C, 71.25; H, 4.98; O, 15.82; S, 7.93. Found: C, 71.25; H, 4.90; O, 15.78; S, 7.65.

Mass spectrum: Theory, 404; Found, 404.

EXAMPLE 10

Preparation of 2-(4-Hydroxyphenyl)-3-(4-methoxybenzoyl)-6-hydroxybenzothiophene

A mixture of 53 g. of the product of Example 9 in dry chloroform was prepared. The mixture was cooled to 10° C., and 75 g. of boron tribromide were added. The mixture was stirred for 24 hours at room temperature. The mixture then was poured into water, the chloroform layer was separated, and the aqueous layer was extracted with additional chloroform which was added to the separated chloroform layer. The resulting chloroform mixture then was filtered, and the filtrate was concentrated to dryness. The residue was dissolved in benzene, the benzene solution was filtered, concentrated to dryness, and the residue was chromatographed on silica using 10 percent ether in benzene as eluant. Those fractions containing material having the same $R_f$ value were combined and rechromatographed on alumina using ether as solvent followed by a mixture of 10 percent methanol in ether. The title compound (5.8 g.) was obtained, melting point 138°–140° C.

Analysis, Calcd. for $C_{22}H_{16}O_4S$: C, 70.20; H, 4.28; O, 17.00. Found: C, 70.46; H, 4.50; O, 16.87.

EXAMPLE 11

Preparation of the Citrate Salt of 2-Phenyl-3-[4-(2-pyrrolidinoethoxy)benzoyl]benzothiophene To 50 g. (0.328 mole) of methyl p-hydroxybenzoate in 250 ml. of anhydrous N,N-dimethylformamide (DMF) were added 68 g. (0.4 mole) of N-(2-chloroethyl)pyrrolidine hydrochloride. To the resulting mixture were added in portions 19.2 g. (0.8 mole) of sodium hydride. The mixture became effervescent. When the effervescence had ceased, the reaction mixture was heated at 80° C. for 72 hours. The excess sodium hydride was decomposed by addition dropwise of 50 ml. of methanol. The solvents then were evaporated from the resulting mixture, and the residue was dissolved in a mixture of ethyl acetate and ice water. The ethyl acetate layer was separated, washed three times with 50 ml. each of aqueous sodium chloride, dried over magnesium sulfate, and evaporated to a dark brown oil. The oil was dissolved in ether, and the ether solution was extracted with 400 ml. of 1N hydrochloric acid. The hydrochloric acid extract then was washed twice with 500 ml. of ether, cooled to 0° C., and rendered alkaline by addition of 250 ml. of 2N sodium hydroxide. The alkaline mixture was extracted with ether, and the ether extract was dried over magnesium sulfate and distilled to give 53 g. (65 percent) of methyl 4-(2-pyrrolidinoethoxy)benzoate as a nearly colorless oil, boiling point 151°–155° C./0.1 mm.

To 150 ml. of methanol were added 30.5 g. (0.122 mole) of the above ester and 61.2 ml. of 2N sodium hydroxide. The mixture was refluxed for 12 hours, cooled, and evaporated to dryness. The resulting white residue was dissolved in water, and the solution was washed several times with ether. The aqueous layer then was acidified with 42 ml. (0.25 mole) of 6N hydrochloric acid. The resulting acidic solution was concentrated to about 300 ml., heated on a steam bath until a clear solution resulted, and then cooled to 5° C. White crystals were collected, washed with ice water and dried in vacuo to obtain 29.1 g. (87.5 percent) of the hydrochloride salt of 4-(2-pyrrolidinoethoxy)benzoic acid, melting point 255°–260° C.

Analysis, Calcd. for $C_{13}H_{18}ClNO_3$: C, 57.46; H, 6.68; N, 5.15; Cl, 13.05 Found: C, 57.24; H, 6.75; N, 5.11; Cl, 13.07.

To 50 ml. of benzene were added 5.0 g. (0.018 mole) of the above benzoic acid and 25 ml. of thionyl chloride (0.35 mole). The mixture was refluxed for two hours with addition of two drops of DMF. The acid dissolved to produce a pale yellow solution. The mixture was evaporated to dryness, and 50 ml. of 1,2-dichloroethane were added. The mixture again was evaporated to dryness. To the resulting white, crystalline, hydrochloride salt were added 150 ml. of 1,2-dichloroethane, 2.4 g. (0.018 mole) of aluminum chloride, and 3.78 g. (0.018 mole) of 2-phenylbenzothiophene. The resulting mixture was a dark solution. An additional 2.4 g. of aluminum chloride were added, and the mixture was stirred overnight. Hydrogen chloride evolved with a resulting red-brown solution. Ice was added to the mixture, and the mixture was evaporated after being rendered alkaline by addition of 5N sodium hydroxide. The resulting residue was dissolved in ethyl acetate, and the ethyl acetate solution was washed with 2N sodium hydroxide and then with water. The ethyl acetate solution was dried over magnesium sulfate, filtered, and evaporated. The residue was chromatographed over silica to obtain 6.2 g. (81 percent) of the free base of the title compound. The free base was converted to the citrate salt by addition of 3.05 g. of citric acid in 60 ml. of methyl ethyl ketone to obtain 8.23 g. of the title compound.

Analysis, Calcd. for $C_{33}H_{33}NO_9S$: C, 63.96; H, 5.37; N, 2.26. Found: C, 63.67; H, 5.25; N, 2.18.

EXAMPLE 12

Preparation of the Citrate Salt of 2-Phenyl-3-[4-(2-pyrrolidinoethoxy)benzoyl]-6-methoxybenzothiophene To 200 ml. of 1,2-dichloroethane were added 6.72 g. (0.035 mole) of 2-pyrrolidinoethoxybenzene (prepared by treating phenol with the hydrochloride salt of 1-pyrrolidino-2-chloroethane in the presence of sodium hydride and anhydrous DMF at 0° C.). The resulting mixture was cooled to 0° C., and excess dry hydrogen chloride was added to convert the amine to the hydrochloride salt. The resulting solution was evaporated to dryness, and the white crystalline residue was suspended in 200 ml. of 1,2-dichloroethane. To the mixture was added the acid chloride derivative prepared from 10.0 g. (0.035 mole) of 2-phenyl-3-carboxyl-6-methoxybenzothiophene. The resulting mixture was cooled to 0° C., and 4.8 g. (0.036 mole) of aluminum chloride were added. The resulting reaction mixture was a light brown solution. An additional 4.8 g. of aluminum chloride were added. A yellow-brown solution resulted with evolution of hydrogen chloride. The mixture was stirred overnight. Ice then was added, and the mixture was rendered alkaline by addition of 5N sodium hydroxide. The mixture then was evaporated, and the residue was dissolved in a mixture of ethyl acetate and water with the aid of a small amount of chloroform. The organic layer was separated and washed with 2N sodium hydroxide. The product was extracted from the organic layer using an excess of 0.05 N hydrochloric acid. The hydrochloric acid extract was washed with ether and then rendered alkaline by addition of 5N sodium hydroxide. The resulting product was extracted into ethyl acetate, and the ethyl acetate solution was dried over magnesium sulfate, filtered, and evaporated to give 6.75 g. of the title compound as the free base which was converted to the citrate salt by treatment with 3.0 g. of citric acid and 60 ml. of acetone. Evaporation of the acetone and trituration of the residue with ether readily gave 8.85 g. (39 percent) of the title compound as a crystalline solid.

Analysis, Calcd. for $C_{34}H_{35}NO_{10}S$: C, 62.85; H, 5.43; N, 2.16; S, 4.94. Found: C, 62.95; H, 5.48; N, 1.99; S, 5.05.

EXAMPLE 13

Preparation of 2-(4-Methoxyphenyl)-3-(4-methoxybenzoyl)benzothiophene.

To 250 ml. of 1,2-dichloroethane were added 15.0 g. (0.0625 mole) of 2-(4-methoxyphenyl)benzothiophene, 10.74 g. (0.063 mole) of anisoyl chloride, and 8.4 g. (0.063 mole) of aluminum chloride. The mixture was maintained at 0° C. for one hour. Thin-layer chromatography (TLC) of the reaction mixture indicated the presence of a trace of the starting benzothiophene. An additional 1.1 g. of anisoyl chloride and 0.8 g. of aluminum chloride were added, and the mixture was stirred for an additional hour. Employing the workup procedure of Example 1, there were obtained 22.7 g. (97 percent) of 2-(4-methoxyphenyl)-3-(4-methoxybenzoyl)-benzothiophene, melting point 124°–126° C.

Analysis Calcd. for $C_{23}H_{18}O_3S$: C, 73.77; H, 4.85; O, 12.82; S, 8.56. Found: C, 73.68; H, 4.95; O, 13.01; S, 8.38.

Mass spectrum: Theory, 374; Found, 374.

EXAMPLE 14

Preparation of 2-(4-Hydroxyphenyl)-3-(4-methoxybenzoyl)benzothiophene.

To 500 ml. of chloroform were added 15.0 g. (0.040 mole) of the benzothiophene product from Example 13. The mixture was maintained at 25° C., and 17.9 g. (0.071 mole) of boron tribromide were added. The mixture was stirred for 36 hours, and water and ice then were added. The chloroform layer was separated, dried over magnesium sulfate, and evaporated to give 15.2 g. of a brown oil. The oil was chromatographed over a 1 × 12 inches silica column using, as gradient, 1500 ml. of benzene and 1500 ml. of 10 percent ethyl acetate in benzene, to obtain 9.21 g. (64 percent) of 2-(4-hydroxyphenyl)-3-(4-methoxybenzoyl)benzothiophene.

EXAMPLE 15

Preparation of the Citrate Salt of 2-[4-(2-Pyrrolidinoethoxy)phenyl]-3-(4-methoxybenzoyl)-benzothiophene.

To 100 ml. of DMF at 0° C. were added 9.2 g. (0.0256 mole) of the benzothiophene from Example 14 and 4.35 g. (0.0256 mole) of N-(2-chloroethyl)pyrrolidine hydrochloride. To the resulting mixture were added 1.44 g. (0.060 mole) of sodium hydride, and the mixture was heated at 70° C. for four hours. TLC showed the presence of starting material, and 0.72 g. of sodium hydride was added to the mixture, and the mixture was heated at 80° C. for one hour. The mixture then was cooled, and ice was added. The DMF was evaporated, and water and ether were added to the residue. The ether layer was separated, washed twice with 50 ml. of 2N sodium hydroxide and then with 50 ml. of aqueous sodium chloride. The ether layer then was dried over potassium carbonate and evaporated to give 9.3 g. (80 percent) of a yellow oil. The yellow oil was dissolved in 50 ml. of hot methyl ethyl ketone, and 4.28 g. (0.02035 mole) of citric acid monohydrate in 50 ml. of hot methyl ethyl ketone were added. Upon cooling of the mixture white crystals formed. The mixture was diluted with 400 ml.

of ether and allowed to stand at 0° C. after which were recovered 11.0 g. (64 percent) of the title compound as white crystals, melting point 86°–92° C.

Analysis, Calcd. for $C_{34}H_{37}NO_{11}S$: C, 61.16; H, 5.59; N, 2.10; O, 26.36; S, 4.80. Found: C, 61.43; H, 5.46; N, 2.26; O, 26.58; S, 4.62.

EXAMPLE 16

Preparation of 2-[4-(2-Pyrrolidinoethoxy)phenyl]-3-(4-methoxybenzoyl)benzothiophene.

To 75 ml. of water were added 3.33 g. (0.005 mole) of the product from Example 15. Some ice was added to the mixture along with 150 ml. of ether, and, gradually, with shaking, 10.0 ml. of 2N sodium hydroxide were added. The ether layer was separated, washed with 25 ml. of saturated aqueous sodium chloride solution, dried over magnesium sulfate, and evaporated to give a pale yellow oil which was dried in vacuo at 40° C. to obtain 2.21 g. (97 percent) of the title compound.

Analysis, Calcd. for $C_{28}H_{27}NO_3S$: C, 73.50; H, 5.95; N, 3.06; S, 7.01. Found: C, 73.35; H, 5.96; N, 3.00; S, 7.06.

EXAMPLE 17

Preparation of the Hydrochloride Salt of 2-[4-(2-Pyrrolidinoethoxy)phenyl]-3-(4-methoxybenzoyl)benzothiophene.

The product from Example 15 (3.33 g.; 0.005 mole) was converted to the corresponding free base compound in accordance with the procedure of Example 16. The resulting product then was dissolved in 50 ml. of methylene chloride. The mixture was cooled to 0° C., and an excess of dry hydrogen chloride was added. The methylene chloride solution then was evaporated, and the residue was dried in vacuo at 40° C. to obtain 2.31 g. (94 percent) of the title compound as a white foam.

EXAMPLE 18

Preparation of 2-[4-(2-Pyrrolidinoethoxy)phenyl]-3-(4-hydroxybenzoyl)benzothiophene.

To 50 ml. of dry DMF were added 1.2 g. (2.6 mmole) of the product from Example 16. Sodium hydride (625 mg.; 26 mmole) was added to the mixture under a nitrogen atmosphere. To the resulting mixture then were slowly added by syringe 620 mg. (10 mmole) of ethyl mercaptan. A vigorous effervescence occurred. When the effervescence had ceased, the reaction mixture was heated at 75° C. in an oil bath for 12 hours. Ethanol (5 ml.) then was added dropwise. The resulting mixture was evaporated to dryness, and the residue was dissolved in a mixture of ethyl acetate and water. The ethyl acetate layer was separated, washed with 50 ml. of aqueous sodium chloride solution, and then repeatedly with 15 ml. portions of 1N hydrochloric acid. The hydrochloric acid extracts were combined, washed with ether, and rendered alkaline by addition of cold 1N sodium hydroxide. The alkaline mixture then was extracted with ethyl acetate, and the ethyl acetate extract, after drying over magnesium sulfate, was evaporated to obtain 0.54 g. of a yellow oil. The yellow oil was chromatographed to obtain 400 mg. of the title compound as a yellow foam.

Mass Spectrum: Theory, 443; Found, 443.

EXAMPLE 19

Preparation of the Citrate Salt of 2-[4-(2-Diethylaminoethoxy)phenyl]-3-(4-methoxybenzoyl)benzothiophene.

Employing the general procedure of Example 15, 4.9 g. (0.014 mole) of 2-(4-hydroxyphenyl)-3-(4-methoxybenzoyl)benzothiophene were treated with sodium hydride and 1-diethylamino-2-chloroethane, and the resulting product was treated with citric acid to obtain 4.8 g. of the title compound, melting point 128°–132° C.

Analysis, Calcd. for $C_{34}H_{37}NO_{10}S$: C, 62.66; H, 5.72; O, 24.55; N, 2.15. Found: C, 62.95; H, 5.46; O, 24.36; N, 2.02.

EXAMPLE 20

Preparation of 2-(4-Hydroxyphenyl)-3-(4-hydroxybenzoyl)benzothiophene.

A mixture of 5.0 g. (0.0134 mole) of 2-(4-methoxyphenyl)-3-(4-methoxybenzoyl)benzothiophene (prepared as in Example 13) and 20 g. of pyridine hydrochloride was prepared. The mixture was treated in accordance with the procedure described in Example 2 to give 4.22 g. (91 percent) of 2-(4-hydroxyphenyl)-3-(4-hydroxybenzoyl)benzothiophene as tan crystals, melting point about 90° C. with softening.

Analysis, Calcd. for $C_{21}H_{14}O_3S$: C, 72.81; H, 4.07; O, 13.86; S, 9.26. Found: C, 73.05; H, 4.27; O, 14.10; S, 8.95.

EXAMPLE 21

Preparation of 2-[4-(2-Pyrrolidinoethoxy)phenyl]-3-[4-(2-pyrrolidinoethoxy)benzoyl]benzothiophene, Dicitrate Salt.

The product from Example 20 was treated with two equivalents of sodium hydride and two equivalents of N-(2-chloroethyl)pyrrolidine in accordance with the method of Example 19 to obtain 16.5 g. of a reddish-brown oil.

A portion of the oil was treated with citric acid, and the crude dicitrate salt was heated in acetone. The resulting suspension was cooled, and ether was added. The ether-acetone mixture separated from the oil. The oil then was dissolved in methanol and allowed to stand at room temperature to obtain crystals of the title compound, melting point 115° C.

Analysis, Calcd. for $C_{45}H_{52}N_2O_{17}S$: C, 58.43; H, 5.67; N, 3.03; O, 29.40. Found: C, 58.20; H, 5.43; N, 2.91; O, 29.54.

EXAMPLE 22

Preparation of 2-(4-Methoxyphenyl)-3-(4-hydroxy-benzoyl)benzothiophene.

To a suspension of 2.9 g. (0.12 mole) of sodium hydride in oil were added 13 g. (0.035 mole) of 2-(4-methoxyphenyl)-3-(4-methoxybenzoyl)benzothiophene (prepared as in Example 13) dissolved in DMF. The resulting mixture then was added to a cold solution of DMF containing 7.5 g. of ethyl mercaptan. The mixture was stirred at 70° C. for two hours and was monitored by TLC until little or no starting material remained. The total reaction time was about two hours. The mixture then was concentrated to dryness, water was added, and the aqueous mixture was acidified and extracted with ethyl acetate. The ethyl acetate extract was washed, dried over magnesium sulfate, and evaporated to a residue. The residue was recrystallized from benzene to obtain 9.1 g. (73 percent) of 2-(4-methoxyphenyl)-3-(4-hydroxybenzyl)benzothiophene, melting point 188°–189° C.

Analysis, Calcd. for $C_{22}H_{16}O_3S$: C, 73.31; H, 4.47; O, 13.32. Found: C, 73.14; H, 4.45; O, 13.54.

EXAMPLE 23

Preparation of the Citrate Salt of 2-(4-Methoxyphenyl)-3-[4-(2-pyrrolidinoethoxy)benzoyl]-benzothiophene.

To 100 ml. of anhydrous DMF were added 10.0 g. (0.028 mole) of the benzothiophene from Example 22 and 4.76 g. (0.028 mole) of N-(2-chloroethyl)pyrrolidine hydrochloride. To the resulting mixture maintained at room temperature then were added 1.7 g. (0.07 mole) of sodium hydride. The mixture became efferverscent. When the effervescence had ceased, the mixture was heated, and heating was continued overnight at 80° C. TLC of the reaction mixture indicated the presence of starting material, and 0.48 g. (0.024 mole) of sodium hydride and 1.70 g. (0.01 mole) of the amine hydrochloride were added. The mixture was maintained at 80° C. for one hour, and 50 ml. of ethanol then were added and DMF was evaporated. The resulting residue was dissolved in a mixture of water and ether. The ether layer was separated and extracted repeatedly with 0.5 N hydrochloric acid. The hydrochloric acid extracts were combined and washed with ether and then rendered alkaline by addition of base. The resulting free base was extracted with ether. The ether layer was dried over magnesium sulfate and evaporated to give about 10.5 g. (83 percent) of the title compound as a free base. The free base was treated with citric acid to obtain 15.0 g. (83 percent) of the title compound, melting point 97°–98° C.

EXAMPLE 24

Preparation of the Citrate Salt of 2-(4-Methoxyphenyl)-3-[4-(2-piperidinoethoxy)benzoyl]-benzothiophene.

A mixture of 3.6 g. (0.01 mole) of 2-(4-methoxyphenyl)-3-(4-hydroxybenzoyl)benzothiophene (prepared as in Example 22) and 0.01 mole of sodium hydride (50 percent dispersion in oil) in DMF was prepared. The mixture was warmed and maintained at 35° C. for 1.5 hours. The mixture then was cooled to room temperature, and 0.01 mole of N-(2-chloroethyl)piperidine was added. The mixture was warmed to 65–70° C. for one hour. Stirring was continued overnight at room temperature. The resulting mixture then was concentrated to dryness. Water was added to the residue, and the aqueous mixture was extracted with ethyl acetate. The ethyl acetate was separated, washed, and evaporated. Citric acid (0.01 mole) in hot acetone was added to the residue. The acetone was evaporated and replaced by methyl ethyl ketone, and the mixture then was cooled to room temperature. The title compound (5.5 g.) was collected as a crystalline compound and vacuum dried, melting point 105–107° C.

Analysis, Calcd. for $C_{35}H_{37}NO_{10}S$: C, 63.34; H, 5.62; N, 2.11; O, 24.10. Found: C, 63.11; H, 5.82; N, 2.34; O, 24.33.

EXAMPLE 25

Preparation of the Citrate Salt of 2-(4-Methoxyphenyl)-3-[4-(2-hexamethyleneiminoethoxy)-benzoyl]benzothiophene.

Employing the procedure of Example 24 on a 0.01 mole scale and using N-(2-chloroethyl)hexamethyleneimine instead of N-(2-chloroethyl)piperidine gave 4.3 g. of the title compound as a crystalline solid.

Analysis, Calcd. for $C_{36}H_{39}NO_{10}S$: C, 63.80; H, 5.80; N, 2.07; O, 23.61. Found: C, 63.62; H, 5.84; N, 2.14; O, 23.33.

EXAMPLE 26

Preparation of the Citrate Salt of 2-(4-Methoxyphenyl)-3-[4-(2-diisopropylaminoethoxy)-benzoyl]benzothiophene.

Employing the procedure of Example 24 on a 0.014 mole scale using 1-chloro-2-diisopropylaminoethane instead of N-(2-chloroethyl)piperidine gave the title compound as a crystalline solid.

Analysis, Calcd. for $C_{36}H_{41}NO_{10}S$: C, 63.61; H, 6.08; N, 2.06; O, 23.54 Found: C, 63.37; H, 6.31; N, 1.84; O, 23.51.

EXAMPLE 27

Preparation of 2-(4-Hydroxyphenyl)-3-[4-(2-pyrrolidinoethoxy)benzoyl]benzothiophene.

The product from Example 23 (10 g.; 0.015 mole) was converted to the free base using 2N sodium hydroxide. The free base product was extracted into ether. The ether was evaporated, and the free base was vacuum dried and dissolved in 100 ml. of DMF. Sodium hydride (3.6 g.; 0.149 mole) was added, and, under nitrogen, 4.65 g. (0.075 mole) of ethyl mercaptan was syringed into the mixture at room temperature. The mixture became effervescent. When the effervescence had ceased, the mixture was heated at 100° C. for four hours. TLC of the reaction mixture after this time indicated that some of the amine side chain was being cleaved. Reaction therefore was discontinued, and the mixture was evaporated. The residue was dissolved in a mixture of ethyl acetate and water, and the resulting mixture was acidified to pH 4 and then rendered alkaline by addition of aqueous sodium bicarbonate solution. The ethyl acetate layer was separated, washed with aqueous sodium chloride solution and evaporated. A brown oil resulted which was purified by chromatography to obtain about 3 g. (14 percent) of the title compound.

EXAMPLE 28

Preparation of the Hydrochloride Salt of 2-(4-Acetoxyphenyl)-3-[4-(2-pyrrolidinoethoxy)benzoyl]benzothiophene.

To 50 ml. of methylene chloride were added 1.1 g. (0.0024 mole) of the product from Example 27. The mixture was cooled to 0° C., and 0.44 g. (0.006 mole) of acetyl chloride was added. The mixture was stirred overnight and then evaporated to dryness to give a white foam. The foam was vacuum dried at 80° C./0.1 mm overnight to give 1.2 g. of the title compound as a pale tan foam.

Analysis, Calcd. for $C_{29}H_{28}ClNO_4S$: C, 66.72; H, 5.41; N, 2.68; O, 12.26; S, 6.14; Cl, 6.79. Found: C, 66.48; H, 5.48; N, 2.61; O, 12.48; S, 5.87; Cl, 7.02.

Employing the foregoing procedure, the following compounds were prepared using the product from Example 27 as starting material:

2-(4-propionyloxyphenyl)-3-[4-(2-pyrrolidinoethoxy)-benzoyl]benzothiophene from propionyl chloride;

2-(4-valeryloxyphenyl)-3-[4-(2-pyrrolidinoethoxy)benzoyl]benzothiophene from valeryl chloride;

2-(4-benzoyloxyphenyl)-3-[4-(2-pyrrolidinoethoxy)benzoyl]benzothiophene from benzoyl chloride;

2-(4-adamantoyloxyphenyl)-3-[4-(2-pyrrolidinoethoxy)-benzoyl]benzothiophene from adamantoyl chloride; and 2-(4-ethoxycarbonyloxyphenyl)-3-[4-(2-pyrrolidinoethoxy)benzoyl]benzothiophene from ethyl orthochloroformate.

EXAMPLE 29

Preparation of 2-(4-Methoxyphenyl)-3-(4-hydroxybenzoyl)-6-methoxybenzothiophene.

To 19.8 g. (0.049 mole) of 2-(4-methoxyphenyl)-3-(4-methoxybenzoyl)-6-methoxybenzothiophene (prepared as in Example 9) in DMF were added 10 g. of a 50 percent oil dispersion of sodium hydride (0.2 mole). The mixture was added to a cold solution of 12.4 g. of ethyl mercaptan in DMF. The resulting mixture was warmed to 65°–70° C. and maintained thereat until the reaction mixture indicated by TLC the absence of starting material. The mixture then was evaporated. Water was added to the residue, and the aqueous mixture was acidified and extracted with ethyl acetate. The ethyl acetate extract was washed and evaporated. The residue was chromatographed on silica initially using 1500 ml. of benzene, then benzene containing 1 percent ethyl acetate, and finally benzene containing 3 percent ethyl acetate, at which time the product was eluted. The product was collected and recrystallized from benzene to obtain 10.7 g. of 2-(4-methoxyphenyl)-3-(4-hydroxybenzoyl)-6-methoxybenzothiophene, melting point 114°–116° C.

Analysis, Calcd. for $C_{23}H_{18}O_4S$: C, 70.75; H, 4.65; O, 16.39 Found: C, 70.88; H, 4.50; O, 16.11.

EXAMPLE 30

Preparation of the Citrate Salt of 2-(4-Methoxyphenyl)-3-[4-(2-pyrrolidinoethoxy)benzoyl]-6-methoxybenzothiophene.

To 150 ml. of DMF containing 1.5 g. of sodium hydride present as a 50 percent oil dispersion (equivalent to 0.03 mole) were added 9.55 g. (0.025 mole) of the benzothiophene from Example 29. The mixture was warmed to 35°–40° C. for 1.5 hours. The mixture then was cooled to room temperature, and 3.34 g. of N-(2-chloroethyl)pyrrolidine in a small amount of DMF were added. The resulting mixture was warmed to 60°–70° C. for one hour and then stirred at room temperature overnight. The mixture was evaporated, and the residue was dissolved in ethyl acetate. The ethyl acetate solution was washed with water several times, dried over magnesium sulfate, and concentrated to an oil. The oil was rinsed several times with hexane to remove residual amounts of the mineral oil. The title compound, in the form of its free base (10.8 g.), was recovered.

Analysis, Calcd. for $C_{29}H_{29}NO_4S$: C, 71.43; H, 5.99; N, 2.87; O, 13.12. Found: C, 71.33; H, 6.29; N, 2.76; O, 13.08.

The above free base (4.4 g.) was dissolved in acetone. The solution was warmed, and a solution of one equivalent of citric acid in acetone was added. The mixture was cooled to room temperature and 3.4 g. of the title compound were recovered, melting point 112°–114° C.

Analysis, Calcd. for $C_{35}H_{37}NO_{11}S$: C, 61.84; H, 5.49; N, 2.06; O, 25.89 Found: C, 61.94; H, 5.51; N, 1.89; O, 25.64.

EXAMPLE 31

Preparation of 2-(4-Hydroxyphenyl)-3-[4-(2-pyrrolidinoethoxy)benzoyl]-6-hydroxybenzothiophene.

A mixture of 16.5 grams of 2-(4-methoxyphenyl)-6-methoxybenzothiophene and 50 grams of pyridine hydrochloride was prepared. The mixture was heated at 220° C. for six hours. The resulting mixture then was poured into an ice-water mixture. The mixture was filtered, and the collected solid was dried in air and recrystallized from methanol to obtain 10.5 grams of 2-(4-hydroxyphenyl)-6-hydroxybenzothiophene, melting point 305°–306° C.

Analysis, Calcd. for $C_{14}H_{10}O_2S$: C, 69.40; H, 4.16; O, 13.21; S, 13.23 Found: C, 69.68; H, 4.41; O, 12.29; S, 12.90.

To 300 ml. of acetone containing 50 mg. of 18-crown-6 ether were added 10.0 grams (0.041 mole) of the above diphenol, 21.0 grams (0.09 mole) of α-bromo-p-chloroacetophenone, and 13.8 grams (0.1 mole) of powdered potassium carbonate. The resulting mixture was refluxed for 18 hours after which time incomplete reaction had occurred. To the mixture were added 4.2 grams of α-bromo-p-chloroacetophenone and 2.76 grams of potassium carbonate in 200 ml. of N,N-dimethylformamide, and the mixture was heated at 100° C. overnight. The resulting mixture became very dark. It was evaporated to dryness, water was added to the residue, and the resulting crystals were filtered. The crystals were washed with water and methanol. The yellow-brown residue was extracted with 300 ml. of hot acetone, and the residue then was recrystallized twice from boiling N,N-dimethylformamide to give 9.1 grams (41 percent) of 2-[4-(p-chlorophenacyloxy)phenyl]-6-(p-chlorophenacyloxy)benzothiophene as almost white crystals, melting point about 210° C.

Analysis, Calcd. for $C_{30}H_{20}Cl_2O_4S$: C, 65.82; H, 3.68; O, 11.69; S, 5.86; Cl, 12.95 Found: C, 66.04; H, 3.55; O, 11.52; S, 5.77; Cl, 13.19 Mass spectrum: Theory, 547; Found, 547.

To 500 ml. of 1,2-dichloroethane were added 9.0 grams (16.4 mmoles) of the above bis-phenacyl ether, 16.4 mmoles of 4-(2-pyrrolidinoethoxy)benzoyl chloride, and 8.8 grams of aluminum chloride. The resulting yellow suspension was stirred for 24 hours and then was refluxed for one hour. The mixture was poured over ice containing 50 ml. of 2N sodium hydroxide. The mixture then was filtered through filter aide to remove insoluble starting material, and the filter cake was washed with methanol which was added to the filtrate. The filtrate was concentrated, and the residue was dissolved in ethyl acetate. The ethyl acetate solution was washed with aqueous sodium chloride and dried over magnesium sulfate. Evaporation of the ethyl acetate afforded 7.6 grams of a semisolid yellow oil which nmr analysis showed to be a mixture of about 80 percent 2-[4-(p-chlorophenylacyloxy)phenyl]-3-[4-(2-pyrrolidinoethoxy)benzoyl]-6-(p-chlorophenacyloxy)benzothiophene and 20 percent starting material. This mixture was used in the next succeeding step without further purification.

To 200 ml. of glacial acetic acid were added 7.6 grams of the above crude product. The mixture was heated to 60° C., and 20 grams of zinc powder were added, the temperature being maintained at 60° C. The reaction mixture was stirred for one hour. The mixture then was filtered through filter aide, and the filtrate was evaporated. The resulting residue was dissolved in a mixture of ethyl acetate and aqueous sodium bicarbonate solution. The ethyl acetate layer was separated, washed with aqueous sodium bicarbonate, and dried over potassium carbonate. The mixture was evaporated to obtain about 5 grams of a yellow oil. The oil was chromatographed over silica gel using as eluant a gradient initially composed of 100 percent ethyl acetate and progressing to a 1:1 mixture of ethyl acetate and methanol. A yellow oil (2.6 grams) of the title compound was recovered.

Analysis, Calcd. for $C_{27}H_{25}NO_4S \cdot H_2O$: C, 67.90; H, 5.70; N, 2.93; O, 16.75 Found: C, 68.56; H, 5.80; N, 3.32; O, 16.87.

EXAMPLE 32

Preparation of
2-(4-Hydroxyphenyl)-3-benzoyl-6-hydroxybenzothiophene-1-oxide.

A mixture of 1.0 gram (3.26 mmoles) of 2-(4-hydroxyphenyl)-3-benzoyl-6-hydroxybenzothiophene in 50 ml. of ethyl acetate was prepared and cooled to 0° C. The mixture was stirred, and 620 mg. (3.59 mmoles) of m-chloroperbenzoic acid were added. The mixture was stirred for one hour and then was allowed to stand overnight under refrigeration. The product was chromatographed rapidly over silica gel in a fritted glass funnel, elution being carried out with a 7:3 mixture of benzene and ethyl acetate followed by pure ethyl acetate to obtain 220 mg. (19 percent) of the title compound. Mass spectrum: Theory, 362; Found, 362.

EXAMPLE 33

Preparation of
2-(4-Chlorophenyl)-3-[4-(2-pyrrolidinoethoxy)benzoyl]benzothiophene.

To 400 ml. of ethanol were added 47.2 grams (0.428 mole) of thiophenol and 24.0 grams (0.428 mole) of potassium hydroxide. The mixture was cooled to 5° C., and 100 grams (0.428 mole) of α-bromo-4-chloroacetophenone were added in small portions. The mixture was stirred and allowed to warm to room temperature and then was stirred overnight. To the resulting mixture then were added 0.5 mole of 1H hydrochloric acid and 2 liters of water. The resulting pale yellow crystals were filtered and recrystallized from methanol to give 87.5 grams (78 percent) of α-(phenylthio)-4-chloroacetophenone, melting point 52°-54° C.

Analysis, Calcd. for $C_{14}H_{11}ClOS$: C, 64.00; H, 4.22; O, 6.09; S, 12.20; Cl, 13.49 Found: C, 64.01; H, 3.93; O, 6.22; S, 12.52; Cl, 12.94.

A mixture of 70 grams (0.267 mole) of the above phenylthio compound and 450 grams of polyphosphoric acid was prepared. The mixture was stirred at 100° C., and then was heated to 190° C. and maintained at the latter temperature for 3 hours. The resulting reaction mixture was poured over 2 liters of an ice-water mixture. Oily crystals were collected, washed with water, and recrystallized from ethyl acetate to obtain 21.30 grams (33 percent) of 2-(4-chlorophenyl)benzothiophene, melting point 193°-194° C.

Analysis, Calcd. for $C_{14}H_9ClS$: C, 68.71; H, 3.71; S, 13.10; Cl, 14.49 Found: C, 68.45; H, 3.93; S, 13.16; Cl, 14.23.

The hydrochloride salt of 4-(2-pyrrolidinoethoxy)-benzoic acid (7.77 grams; 0.028 mole) was converted to its corresponding acid chloride. To the acid chloride then were added 7.0 grams (0.028 mole) of the above benzothiophene and 250 ml. of 1,2-dichloroethane. A white suspension resulted. The mixture was cooled to b 0° to 10° C. and was treated gradually with 7.6 grams (0.57 mole) of aluminum chloride, giving rise to a brownish-yellow solution. The mixture was stirred at 0°-25° C. overnight, and then was poured over a mixture of 200 ml. of ice and 75 ml. of 5N sodium hydroxide. The resulting mixture was evaporated to near dryness, and the residue was dissolved in chloroform. The chloroform solution was washed with water and evaporated, and the residue was heated with a mixture of 200 ml. of methanol and 15 ml. of 5N sodium hydroxide. The mixture then was evaporated to dryness, and the residue was dissolved in a mixture of chloroform and water. The chloroform layer was separated, dried over magnesium sulfate, and evaporated to an oil. A small amount of ethyl acetate was added, and the resulting mixture was scratched. Crystals formed and were collected. The mother liquor filtrate was concentrated and chromatographed to obtain 11.5 grams of crystals which were recrystallized from ethyl ether to give 6.63 grams (50 percent) of the title compound, melting point 97°-98° C.

Analysis, Calcd. for $C_{27}H_{24}ClNO_2S$: C, 70.19; H, 5.24; Cl, 7.67; N, 3.03; O, 6.93; S, 6.94 Found: C, 70.30; H, 5.48; Cl, 7.73; N, 2.93; O, 6.92; S, 6.85.

The compounds of this invention are tested for antifertility activity in accordance with the following procedure:

Fifty young adult virgin female rats weighing 200-230 g. each are separated into ten groups of five each. One of the groups serves as the control group and the other nine groups as experimental groups, each such experimental group receiving test compound at a particular dose level. The test compound for each group of five rats is prepared in corn oil such that the daily administration is in 0.1 ml. of vehicle. The designated quantity of the test compound in the vehicle is administered to each rat within the defined group subcutaneously (sc) daily. The control group receives only the vehicle. Administration of the vehicle or the combination of test compound and vehicle is continued on a daily basis for 15 days. On the 5th day of treatment, two adult male rats weighing at least 250 g. each are added to each group, and cohabitation is continued until the 15th day at which time the male rats are withdrawn from the group. Each group of female rats then is maintained for an additional seven days after which the rats are sacrificed and examined for the presence of viable or resorbing fetuses.

The number of animals that exhibit evidence of pregnancy over the number of animals in the group is the pregnancy ratio. A compound is considered active when the ratio is 0/5 or 1/5. A ratio of 2/5 constitutes marginal activity, and anything higher is inactive.

The Table I following illustrates the antifertility activity of compounds of this invention.

Table I
Antifertility Activity
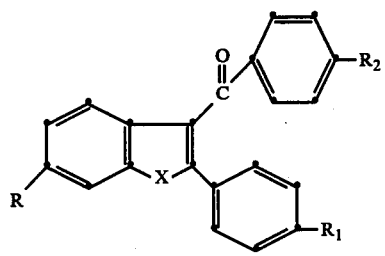
| Compound | | | | Dose | Pregnancy Ratio |
|---|---|---|---|---|---|
| R | $R_1$ | $R_2$ | X | mg./day | P/5 P= |
| —OH | H | H | S | 5.0 | 0 |
|  |  |  |  | 1.0 | 3 |
|  |  |  |  | 0.5 | 2 |
|  |  |  |  | 0.1 | 3 |
| H | H | —OH | S | 5.0 | 0 |
|  |  |  |  | 1.0 | 0 |
|  |  |  |  | 0.5 | 3 |
|  |  |  |  | 0.1 | 4 |
| —OCH$_3$ | H | —OCH$_3$ | S | 5.0 | 1 |
| —OH | H | —OH | S | 5.0 | 0 |
|  |  |  |  | 1.0 | 3[a] |
| —OH | —OH | H | S | 5.0 | 0 |
|  |  |  |  | 1.0 | 0 |
|  |  |  |  | 0.5 | 0 |
|  |  |  |  | 0.1 | 0 |
|  |  |  |  | 0.05 | 5 |
| —OH | —OH | —OCH$_3$ | S | 5.0 | 0 |
|  |  |  |  | 1.0 | 3 |
| H | —OC$_2$H$_4$—N[b] | —OCH$_3$ | S | 1.0 | 0 |
|  |  |  |  | 0.5 | 0 |
|  |  |  |  | 0.1 | 5 |
|  |  |  |  | 0.05 | 4 |
| H | —OC$_2$H$_4$N(C$_2$H$_5$)$_2$[b] | —OCH$_3$ | S | 5.0 | 0 |
|  |  |  |  | 1.0 | 2 |
|  |  |  |  | 0.5 | 2 |
|  |  |  |  | 0.1 | 3 |
| H | —OC$_2$H$_4$N | —OC$_2$H$_4$N[c] | S | 1.0 | 0 |
|  |  |  |  | 0.5 | 4 |
|  |  |  |  | 0.1 | 5 |
| H | —OCH$_3$ | —OC$_2$H$_4$N[b] | S | 1.0 | 0 |
|  |  |  |  | 0.5 | 0 |
|  |  |  |  | 0.1 | 0 |
|  |  |  |  | 0.05 | 5 |
|  |  |  |  | 0.01 | 2 |
| H | H | —OC$_2$H$_4$N[b] | S | 1.0 | 0 |
|  |  |  |  | 0.5 | 0 |
| H | —OC$_2$H$_4$N[d] | —OCH$_3$ | S | 1.0 | 0 |
|  |  |  |  | 0.5 | 0 |
|  |  |  |  | 0.1 | 1[a] |
|  |  |  |  | 0.05 | 4 |
|  |  |  |  | 0.01 | 3[a] |
| H | —OC$_2$H$_4$N | —OCH$_3$ | S | 1.0 | 0 |
|  |  |  |  | 0.5 | 0[a] |
|  |  |  |  | 0.1 | 3 |
|  |  |  |  | 0.1 | 2 |
|  |  |  |  | 0.05 | 5 |
| —OCH$_3$ | —OCH$_3$ | —OC$_2$H$_4$N[b] | S | 0.5 | 0 |
|  |  |  |  | 0.1 | 0 |

Table I-continued
Antifertility Activity

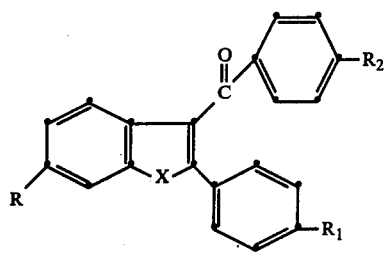

| Compound | | | | Dose | Pregnancy Ratio |
|---|---|---|---|---|---|
| R | $R_1$ | $R_2$ | X | mg./day | P/5 P= |
| H | —OH | —OC$_2$H$_4$N⟨pyrrolidine⟩ | S | 0.05<br>0.01 | 0<br>4 |
| H | —O—CO—CH$_3$ | —OC$_2$H$_4$N⟨pyrrolidine⟩[d] | S | 0.1<br>0.05 | 2<br>2 |
| —OCH$_3$ | H | —OC$_2$H$_4$N⟨pyrrolidine⟩[b] | S | 0.5<br>0.1 | 0<br>4 |
| H | —OCH$_3$ | —OC$_2$H$_4$N⟨piperidine⟩[b] | S | 0.1<br>0.05<br>0.01 | 2<br>1<br>3 |
| H | —OCH$_3$ | —OC$_2$H$_4$N⟨azepane⟩[b] | S | 0.1 | 1 |
| H | —OCH$_3$ | —OC$_2$H$_4$N—[CH(CH$_3$)$_2$]$_2$[b] | S | 0.01<br>0.05<br>0.01 | 2<br>3<br>4 |
| H | Cl | —OC$_2$H$_4$N⟨pyrrolidine⟩ | S | 0.1 | 1 |
| H | —O—CO—CH$_2$CH$_3$ | —OC$_2$H$_4$N⟨pyrrolidine⟩[d] | S | 1.0<br>0.1<br>0.05 | 0<br>0<br>0<br>1 |
| H | —O—CO—O—CH$_2$CH$_3$ | —OC$_2$H$_4$N⟨pyrrolidine⟩[d] | S | 1.0<br>0.1<br>0.05 | 0<br>0 |
| H | —O—CO—(CH$_2$)$_3$CH$_3$ | —OC$_2$H$_4$N⟨pyrrolidine⟩[d] | S | 1.0<br>0.1<br>0.05 | 0<br>0<br>3 |
| H | —O—CO—C$_6$H$_5$ | —OC$_2$H$_4$N⟨pyrrolidine⟩[d] | S | 1.0<br>0.1<br>0.05 | 0<br>0<br>2 |

Table I-continued

Antifertility Activity

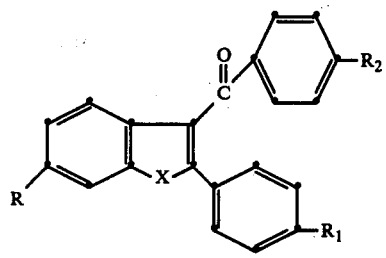

| Compound | | | | Dose | Pregnancy Ratio |
|---|---|---|---|---|---|
| R | R₁ | R₂ | X | mg./day | P/5 P= |
| H | —O—CO-adamantyl | | S | 1.0 | 0 |
| | | | | 0.1 | 0 |
| | —OC₂H₄N⟨ ⟩[d] | | | 0.05 | 0 |

Footnotes:
[a]Pregnancy ratio is P/4.
[b]Citrate salt.
[c]Dicitrate salt.
[d]Hydrochloride salt.

Certain of the compounds of this invention, generally those benzothiophenes in which R₂ is

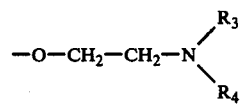

also exhibit activity in the suppression of the growth of mammary tumors in females. This activity is demonstrated by the following procedure in which, for illustrative purposes only, female rats were used, exemplifying tumor-susceptible mammals. This procedure was carried out as follows:

Mammary tumors were produced in female rats by administering 7,12-dimethylbenz-[α]anthracene (DMBA). Rats which were 55 days old were administered a single feeding by gavage of 12 mg. of DMBA. About 6 weeks after DMBA administration, the mammary glands were palpated at weekly intervals for the appearance of tumors. Whenever one or more tumors appeared in an animal and had grown to the size of about 1 cm. in diameter, that animal was selected for experimentation. The test compound was dissolved or suspended in corn oil, and the solution or suspension was administered daily subcutaneously. Every experiment included a group of control rats having tumors and treated on a daily basis with the corn oil vehicle. The tumors were measured before the start of the experiments, and the largest and smallest diameters were recorded. During the treatment with the test compounds, the tumors were measured at weekly intervals. An attempt was made to uniformly distribute the various sizes of tumors in the treated and control groups such that one group did not start with rats having tumors which, on the average, were significantly larger than those of any other group. After measurements were taken, the volume of each tumor was calculated using the formula $V = 4/3\, a\pi b$ in which V is the volume of an oblate spheroid (tumor) in mm³, and a and b are the major and minor semiaxes, respectively. Change in tumor volume was analyzed for its significance using Dunkin's Multiple Range Test. The results of this procedure are shown in Table II following.

Table II

Anti-Tumor Activity

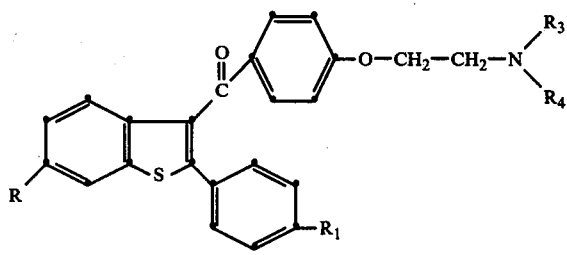

| Test | R | R₁ | —N⟨R₃/R₄ | Dose mg./Kg./day | No. of Rats | Length of Treatment, Days | Mean Change in Tumor Volume, mm³[c] |
|---|---|---|---|---|---|---|---|
| I | | Control (corn oil) | | — | 21 | 18 | +908.0 |
| | H | —OCH₃ | pyrrolidino[a] | 3.6 | 13 | 18 | −280.2 |
| II | | Control (corn oil) | | — | 10 | 14 | +3385.9 |
| | H | —OCH₃ | pyrrolidino[a] | 6.0 | 10 | 14 | +1009.5 |

Table II-continued
Anti-Tumor Activity

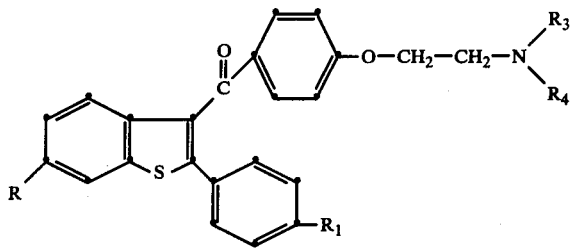

| Test | R | $R_1$ | $-N\binom{R_3}{R_4}$ | Dose mg./Kg./day | No. of Rats | Length of Treatment, Days | Mean Change in Tumor Volume, mm$^{3c}$ |
|---|---|---|---|---|---|---|---|
| | H | $-O\overset{O}{\underset{\|}{C}}-CH_3$ | pyrrolidino[b] | 6.0 | 8 | 14 | +1726.4 |
| III | | Control (corn oil) | | — | 8 | 14 | +562.1 |
| | H | $-OCH_3$ | pyrrolidino[a] | 4.5 | 8 | 14 | +83.5 |
| | H | $-OCH_3$ | piperidino[a] | 6.0 | 8 | 14 | −52.6 |
| IV | | Control (corn oil) | | — | 6 | 28 | +7930.0 |
| | −OH | −OH | pyrrolidino | 0.6 | 6 | 28 | +3320.0 |
| V | | Control (corn oil) | | — | 5 | 28 | +1825.0 |
| | −OH | −OH | pyrrolidino | 1.5 | 5 | 28 | +520.8 |

[a] Citrate salt.
[b] Hydrochloride salt.
[c] In all tests the control results are significantly different from the results obtained from the test compounds at the P<.05 level using Duncan's Multiple Range Test.

As indicated from the above, compounds of this invention are active in suppressing mammary tumor growth.

We claim:

1. A compound of the formula

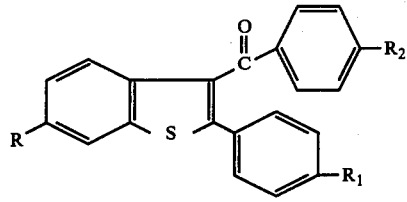

in which R is hydroxyl; $R_1$ is hydrogen, hydroxyl, $C_1$-$C_5$ alkoxy, or

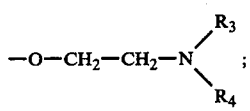

$R_2$ is hydrogen; and $R_3$ and $R_4$ independently are $C_1$-$C_4$ alkyl, or $R_3$ and $R_4$ taken together with the nitrogen to which they are bonded constitute a heterocyclic ring selected from the group consisting of pyrrolidino, piperidino, hexamethyleneimino, or morpholino; and pharmaceutically acceptable non-toxic acid addition salts of those compounds in which $R_1$ is

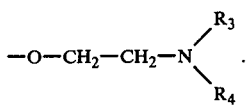

2. A compound of the formula

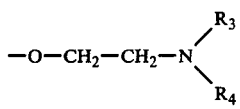

in which R is hydrogen, hydroxyl, or $C_1$-$C_5$ alkoxy; $R_1$ is hydrogen, $C_1$-$C_5$ acyloxy, $C_1$-$C_5$ alkoxycarbonyloxy, benzoyloxy, adamantoyloxy, chloro, bromo, or $$-O-CH_2-CH_2-N\binom{R_3}{R_4};$$

$R_2$ is hydroxyl; and $R_3$ and $R_4$ independently are $C_1$-$C_4$ alkyl, or $R_3$ and $R_4$ taken together with the nitrogen to which they are bonded constitute a heterocyclic ring selected from the group consisting of pyrrolidino, piperidino, hexamethyleneimino, or morpholino; and pharmaceutically acceptable non-toxic acid addition salts of those compounds in which $R_1$ is $$-O-CH_2-CH_2-N\binom{R_3}{R_4}.$$

3. A compound of the formula

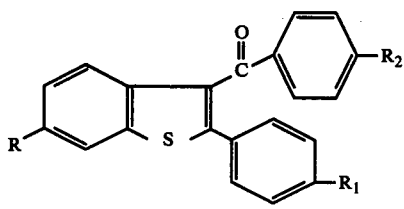

in which R is hydroxyl; $R_1$ is hydroxyl; and $R_2$ is $C_1$-$C_5$ alkoxy.

4. Compound of claim 1, in which $R_1$ is hydroxyl.

5. A compound of the formula

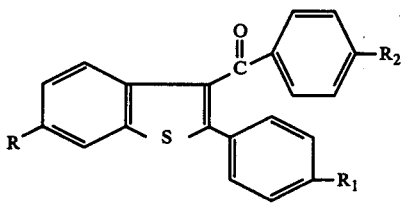

in which R is hydrogen, hydroxyl, or $C_1$-$C_5$ alkoxy; $R_1$ is hydroxyl; and $R_2$ is

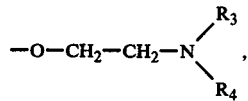

in which $R_3$ and $R_4$ taken together with the nitrogen to which they are bonded constitute a pyrrolidino ring; and pharmaceutically acceptable non-toxic acid addition salts of such compounds.

6. Compound of claim 2, in which $R_1$ is

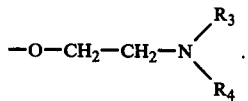

7. Compound of claim 6, in which $R_3$ and $R_4$ taken together with the nitrogen to which they are bonded constitute a pyrrolidino function.

8. Compound of claim 7, in which R is hydrogen.

9. Compound of claim 5, in which R is hydrogen.

10. Compound of claim 5, in which R is hydroxyl.

* * * * *